United States Patent
Gillies

(10) Patent No.: US 11,492,383 B2
(45) Date of Patent: Nov. 8, 2022

(54) LIGHT CHAIN IMMUNOGLOBULIN FUSION PROTEINS AND METHODS OF USE THEREOF

(76) Inventor: Stephen D. Gillies, Carlisle, MA (US)

(*) Notice: Subject to any disclaimer, the term of this patent is extended or adjusted under 35 U.S.C. 154(b) by 368 days.

(21) Appl. No.: 14/129,133

(22) PCT Filed: Jun. 24, 2012

(86) PCT No.: PCT/US2012/043914
§ 371 (c)(1),
(2), (4) Date: May 21, 2014

(87) PCT Pub. No.: WO2012/178137
PCT Pub. Date: Dec. 27, 2012

(65) Prior Publication Data
US 2014/0294758 A1    Oct. 2, 2014

Related U.S. Application Data

(60) Provisional application No. 61/501,161, filed on Jun. 24, 2011.

(51) Int. Cl.
  C07K 14/55    (2006.01)
  C07K 16/30    (2006.01)
  C07K 16/28    (2006.01)
  C07K 16/46    (2006.01)

(52) U.S. Cl.
  CPC .......... *C07K 14/55* (2013.01); *C07K 16/2809* (2013.01); *C07K 16/30* (2013.01); *C07K 16/3084* (2013.01); *C07K 16/468* (2013.01); *C07K 2317/31* (2013.01); *C07K 2317/51* (2013.01); *C07K 2317/515* (2013.01); *C07K 2317/622* (2013.01); *C07K 2317/732* (2013.01); *C07K 2317/734* (2013.01); *C07K 2317/94* (2013.01); *C07K 2319/00* (2013.01)

(58) Field of Classification Search
  CPC ............ C07K 2319/75; C07K 2317/32; C07K 2319/00; C07K 14/55
  See application file for complete search history.

(56) References Cited

U.S. PATENT DOCUMENTS

| | | | |
|---|---|---|---|
| 5,852,183 A | 12/1998 | Maeda et al. | |
| 6,028,176 A | 2/2000 | Greve et al. | |
| 6,313,272 B1 | 11/2001 | Greve et al. | |
| 6,335,426 B1 | 1/2002 | Shanafelt et al. | |
| 6,455,043 B1 | 9/2002 | Grillo-Lopez | |
| 6,617,135 B1 * | 9/2003 | Gillies | A61K 38/193 435/252.3 |
| 6,955,807 B1 * | 10/2005 | Shanafelt | C07K 14/55 424/85.2 |
| 7,105,653 B2 | 9/2006 | Shanafelt et al. | |
| 7,148,321 B2 | 12/2006 | Gillies et al. | |
| 7,169,904 B2 | 1/2007 | Gillies et al. | |
| 7,261,890 B2 | 8/2007 | Krah, III et al. | |
| 7,371,371 B2 | 5/2008 | Epstein et al. | |
| 7,423,123 B2 | 9/2008 | Bosivert et al. | |
| 7,465,447 B2 | 12/2008 | Gillies et al. | |
| 7,514,073 B2 | 4/2009 | Epstein et al. | |
| 7,582,288 B2 | 9/2009 | Gillies et al. | |
| 7,691,606 B2 | 4/2010 | Klein et al. | |
| 7,803,361 B2 | 9/2010 | Epstein et al. | |
| 2002/0146388 A1 | 10/2002 | Gillies et al. | |
| 2002/0193570 A1 | 12/2002 | Gillies et al. | |
| 2003/0044423 A1 | 3/2003 | Gillies et al. | |
| 2003/0049227 A1 | 3/2003 | Gillies et al. | |
| 2003/0139365 A1 | 7/2003 | Lo et al. | |
| 2003/0166163 A1 | 9/2003 | Gillies et al. | |
| 2004/0033210 A1 | 2/2004 | Gillies et al. | |
| 2004/0053366 A1 | 3/2004 | Lo et al. | |
| 2004/0072299 A1 * | 4/2004 | Gillies | C07K 16/30 530/391.1 |
| 2004/0203100 A1 | 10/2004 | Gillies et al. | |
| 2005/0069521 A1 | 3/2005 | Gillies et al. | |
| 2005/0192211 A1 | 9/2005 | Gillies et al. | |
| 2005/0202538 A1 | 9/2005 | Gillies et al. | |
| 2005/0226885 A1 * | 10/2005 | Soegaard | C07K 14/47 424/184.1 |
| 2006/0142196 A1 | 6/2006 | Klein et al. | |
| 2006/0263856 A1 | 11/2006 | Gillies et al. | |
| 2007/0009538 A1 | 1/2007 | Lo et al. | |
| 2007/0104689 A1 | 5/2007 | Gillies et al. | |

(Continued)

FOREIGN PATENT DOCUMENTS

| | | |
|---|---|---|
| EP | 0 998 305 A2 | 5/2000 |
| EP | 1 572 748 B1 | 6/2010 |

(Continued)

OTHER PUBLICATIONS

Bowie et al. Deciphering the message in protein sequence: tolerance to amino acid substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology. 111:2129-2138, 1990.*
Lazar et al. Transforming Growth Factor alpha: Mutation of Aspartic Acid 47 and Leucine 48 Results in Different Biological Activities. Molecular and Cellular Biology, 8:1247-1252, 1988.*
Bork. Powers and pitfalls in sequence analysis: the 70% hurdle. Genome Research, 2000; 10:398-400.*
Gillies et al. Journal of Immunology, 144:1382-1396 (Year: 1990).*
Elias et al. Cancer Research, 1990; 50:4154-4159 (Year: 1990).*

(Continued)

*Primary Examiner* — Vanessa L. Ford
*Assistant Examiner* — Sandra Dillahunt
(74) *Attorney, Agent, or Firm* — Wolf, Greenfield & Sacks, P.C.

(57) ABSTRACT

Provided are recombinant antibodies comprising one or more peptides fused to the C-terminus of the light chain constant region. Recombinant immunocytokines comprising a cytokine fused to the C-terminus of the light chain constant region are described and shown to be surprisingly active.

8 Claims, 12 Drawing Sheets

Specification includes a Sequence Listing.

(56) References Cited

U.S. PATENT DOCUMENTS

| | | | |
|---|---|---|---|
| 2007/0178098 A1 | 8/2007 | Way et al. | |
| 2008/0025947 A1* | 1/2008 | Gillies | A61P 43/00 424/85.2 |
| 2010/0086972 A1 | 4/2010 | Rehm | |
| 2010/0239582 A1* | 9/2010 | Humphreys | C07K 16/00 424/136.1 |
| 2011/0091413 A1 | 4/2011 | Epstein et al. | |
| 2011/0142884 A1 | 6/2011 | Onyuksel et al. | |
| 2012/0020966 A1* | 1/2012 | Barbas, III | C07K 14/515 424/134.1 |
| 2014/0294758 A1 | 10/2014 | Gillies et al. | |

FOREIGN PATENT DOCUMENTS

| | | | |
|---|---|---|---|
| WO | WO 96/32471 A2 | 10/1996 | |
| WO | WO 97/49424 A1 | 12/1997 | |
| WO | WO 99/04820 A2 | 2/1999 | |
| WO | WO 99/24565 A1 | 5/1999 | |
| WO | WO 99/50461 A1 | 10/1999 | |
| WO | WO 00/04041 A2 | 1/2000 | |
| WO | WO 00/41724 A1 | 7/2000 | |
| WO | WO 00/42074 A1 | 7/2000 | |
| WO | WO 01/10205 A1 | 2/2001 | |
| WO | WO 01/42308 A2 | 6/2001 | |
| WO | WO 2001/58957 A2 | 8/2001 | |
| WO | WO 01/64754 A1 | 9/2001 | |
| WO | WO 02/11762 A2 | 2/2002 | |
| WO | WO 02/26249 A2 | 4/2002 | |
| WO | WO 03/018635 A1 | 3/2003 | |
| WO | WO 03/066830 A2 | 8/2003 | |
| WO | WO 2004/055056 A1 | 7/2004 | |
| WO | WO 2004/059285 A2 | 7/2004 | |
| WO | WO 2004/060295 A2 | 7/2004 | |
| WO | WO 2004/078938 A2 | 9/2004 | |
| WO | WO 2005/035582 A1 | 4/2005 | |
| WO | WO 2005/053741 A1 | 6/2005 | |
| WO | WO-2005086798 A2 * | 9/2005 | C07K 14/55 |
| WO | WO 2005086798 A2 * | 9/2005 | C07K 14/55 |
| WO | WO 2006/020266 A2 | 2/2006 | |
| WO | WO 2006/089141 A2 | 8/2006 | |
| WO | WO 2007/005605 A2 | 1/2007 | |
| WO | WO 2007/005874 A2 | 1/2007 | |
| WO | WO 2007048022 A2 * | 4/2007 | A61K 47/48484 |
| WO | WO 2007/084321 A2 | 7/2007 | |
| WO | WO 2007/113301 A1 | 10/2007 | |
| WO | WO 2008/060367 A1 | 5/2008 | |
| WO | WO 2008/137475 A2 | 11/2008 | |
| WO | WO 2008/142303 A2 | 11/2008 | |
| WO | WO 2009/014745 A1 | 1/2009 | |
| WO | WO 2009/086514 A1 | 7/2009 | |
| WO | WO 2009/095478 A1 | 8/2009 | |
| WO | WO 2009/117706 A2 | 9/2009 | |
| WO | WO 2009/120186 A1 | 10/2009 | |
| WO | WO 2009/138519 A1 | 11/2009 | |
| WO | WO 2009/140124 A1 | 11/2009 | |
| WO | WO 2010/036959 A2 | 4/2010 | |
| WO | WO 2010/037831 A1 | 4/2010 | |
| WO | WO 2010/077634 A1 | 7/2010 | |
| WO | WO 2010/089411 A2 | 8/2010 | |
| WO | WO 2010/099536 A2 | 9/2010 | |
| WO | WO 2010/117448 A2 | 10/2010 | |
| WO | WO 2010/125162 A1 | 11/2010 | |
| WO | WO 2010/142952 A2 | 12/2010 | |
| WO | WO 2011/042398 A1 | 4/2011 | |
| WO | WO 2011/066389 A1 | 6/2011 | |
| WO | WO 2011/083140 A1 | 7/2011 | |
| WO | WO 2011/083141 A2 | 7/2011 | |
| WO | WO 2011/098762 A2 | 8/2011 | |
| WO | WO 2011/100538 A1 | 8/2011 | |
| WO | WO 2011/121040 A1 | 10/2011 | |
| WO | WO 2011/161266 A1 | 12/2011 | |
| WO | WO 2012170072 A1 * | 12/2012 | C07K 16/2887 |

OTHER PUBLICATIONS

Montano et al. Journal of Immunology, 2002; 168:224-231 (Year: 2002).*

Gillies et al. Enhancement of antibody-dependent cytotoxicity with a chimeric anti-GD2 antibody. Journal of Immunology, 1990; 144: 1382-1396 (Year: 1990).*

Elias et al. Phase I Clinical Comparative Study of Monoclonal Antibody KS1/4 and KS1/4- Methotrexate Imniunconjugate in Patients with Non-Small Cell Lung Carcinoma/Cancer Research, 1990; 50:4154-4159. (Year: 1990).*

Janeway et al. Immunobiology: The Immune System in Health and Disease. 5th edition, New York: Garland Science; 2001. (Year: 2200).*

Bowie et al. Science, 1990, 247:1306-1310 (Year: 1990).*

Burgess et al. J. Cell Biol. 111:2129-2138, 1990 (Year: 1990).*

Lazar et al. Mol. Cell. Biol., 8:1247-1252, 1988 (Year: 1988).*

Bork. Genome Research, 2000; 10:398-400 (Year: 2000).*

Assier et al., NK cells and polymorphonuclear neutrophils are both critical for IL-2-induced pulmonary vascular leak syndrome. J Immunol. Jun. 15, 2004;172(12):7661-8.

Becker et al., An antibody-interleukin 2 fusion protein overcomes tumor heterogeneity by induction of a cellular immune response. Proc Natl Acad Sci U S A. Jul. 23, 1996;93(15):7826-31.

Becker et al., Eradication of human hepatic and pulmonary melanoma metastases in SCID mice by antibody-interleukin 2 fusion proteins. Proc Natl Acad Sci U S A. Apr. 2, 1996;93(7):2702-7.

Becker et al., T cell-mediated eradication of murine metastatic melanoma induced by targeted interleukin 2 therapy. J Exp Med. May 1, 1996;183(5):2361-6.

Gan et al., Specific enzyme-linked immunosorbent assays for quantitation of antibody-cytokine fusion proteins. Clin Diagn Lab Immunol. Mar. 1999;6(2):236-42.

Gillies et al., An anti-CD20-IL-2 immunocytokine is highly efficacious in a SCID mouse model of established human B lymphoma. Blood. May 15, 2005;105(10):3972-8. Epub Feb. 3, 2005.

Gillies et al., Antibody-IL-12 fusion proteins are effective in SCID mouse models of prostate and colon carcinoma metastases. J Immunol. Jun. 15, 1998;160(12):6195-203.

Gillies et al., High-level expression of chimeric antibodies using adapted cDNA variable region cassettes. J Immunol Methods. Dec. 20, 1989;125(1-2): 191-202.

Gillis et al., T cell growth factor: parameters of production and a quantitative microassay for activity. J Immunol. Jun. 1978;120(6):2027-32.

Gillies, A new platform for constructing antibody-cytokine fusion proteins (immunocytokines) with improved biological properties and adaptable cytokine activity. Protein Eng Des Sel. Oct. 2013;26(10):561-9. doi:10.1093/protein/gzt045. Epub Sep. 10, 2013.

Gillies et al., A low-toxicity IL-2-based immunocytokine retains antitumor activity despite its high degree of IL-2 receptor selectivity. Clin Cancer Res. Jun. 1, 2011;17(11):3673-85. doi: 10.1158/1078-0432.CCR-10-2921. Epub Apr. 29, 2011.

Hank et al., Activation of human effector cells by a tumor reactive recombinant anti-ganglioside GD2 interleukin-2 fusion protein (ch14.18-IL2). Clin Cancer Res. Dec. 1996;2(12):1951-9.

Isaacs et al., Therapy with monoclonal antibodies. II. The contribution of Fc gamma receptor binding and the influence of C(H)1 and C(H)3 domains on in vivo effector function. J Immunol. Oct. 15, 1998;161(8):3862-9.

Kanai et al., Identification of two allelic IgG1 C(H) coding regions (Cgamma1) of cat. Vet Immunol Immunopathol. Jan. 31, 2000;73(1):53-62.

Mueller et al., Enhancement of antibody-dependent cytotoxicity with a chimeric anti-GD2 antibody. J Immunol. Feb. 15, 1990;144(4):1382-6.

Orcutt et al., A modular IgG-scFv bispecific antibody topology. Protein Eng Des Sel. Apr. 2010;23(4):221-8. doi: 10.1093/protein/gzp077. Epub Dec. 17, 2009.

Osenga et al., A phase I clinical trial of the hu14.18-IL2 (EMD 273063) as a treatment for children with refractory or recurrent neuroblastoma and melanoma: a study of the Children's Oncology Group. Clin Cancer Res. Mar. 15, 2006;12(6):1750-9.

(56) References Cited

OTHER PUBLICATIONS

Pancook et al., Eradication of established hepatic human neuroblastoma metastases in mice with severe combined immunodeficiency by antibody-targeted interleukin-2. Cancer Immunol Immunother. Feb. 1996;42(2):88-92.

Sabzevari et al., A recombinant antibody-interleukin 2 fusion protein suppresses growth of hepatic human neuroblastoma metastases in severe combined immunodeficiency mice. Proc Natl Acad Sci USA. Sep. 27, 1994;91(20):9626-30.

Wagner et al., Horse cytokine/IgG fusion proteins—mammalian expression of biologically active cytokines and a system to verify antibody specificity to equine cytokines. Vet Immunol Immunopathol. May 1, 2005;105(1-2):1-14.

Baum et al., Therapy with CD7 monoclonal antibody TH-69 is highly effective for xenografted human T-cell ALL. Br J Haematol. Nov. 1996;95(2):327-38.

Boll et al., The fully human anti-CD30 antibody 5F11 activates NF-κB and sensitizes lymphoma cells to bortezomib-induced apoptosis. Blood. 2005;106:1839-1842.

Collins et al., Identification of specific residues of human interleukin 2 that affect binding to the 70-kDa subunit (p70) of the interleukin 2 receptor. Proc Natl Acad Sci U S A. Oct. 1988;85(20):7709-13.

Foyil et al. Anti-CD30 Antibodies for Hodgkin lymphoma. Curr Hematol Malig Rep. Jul. 2010;5(3): 140-7.

Hailey et al., Neutralizing Anti-Insulin-like Growth Factor Receptor 1 Antibodies Inhibit Receptor Function and Induce Receptor Degradation in Tumor Cells. Mol Cancer Ther 2002;1:1349-1353.

Heaton et al., Human interleukin 2 analogues that preferentially bind the intermediate-affinity interleukin 2 receptor lead to reduced secondary cytokine secretion: implications for the use of these interleukin 2 analogues in cancer immunotherapy. Cancer Res. Jun. 1, 1993;53(11):2597-602.

Ho et al., Glypica-3: a new target for cancer immunotherapy. Eur J Cancer. Feb. 2011;47(3): 333-338. Author manuscript.

Hu et al., Generation of low-toxicity interleukin-2 fusion proteins devoid of vasopermeability activity. Blood. Jun. 15, 2003;101(12):4853-61. Epub Feb. 27, 2003.

Martinelli et al., Anti-epidermal growth factor receptor monoclonal antibodies in cancer therapy. Clin Exp Immunol. Oct. 2009; 158(1): 1-9.

Niwa et al., Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma. Cancer Res. Mar. 15, 2004;64(6):2127-33.

Quintás-Cardama et al., Investigational immunotherapeutics for B-cell malignancies. J Clin Oncol. Feb. 10, 2010;28(5):884-92. doi: 10.1200/JCO.2009.22.8254. Epub Jan. 4, 2010.

Ryan et el. Antibody targeting of B-cell maturation antigen on malignant plasma cells. Mol Cancer Ther. Nov. 2007;6(11):3009-18.

Weiner et al., Antibody-based immunotherapy of cancer. Cell. Mar. 16, 2012; 148(6): 1081-4. doi: 10.1016/j.cell.2012.02.034.

\* cited by examiner

LIGHT CHAIN IMMUNOGLOBULIN FUSION PROTEINS AND METHODS OF USE THEREOF

RELATED APPLICATIONS

This application is a US National Stage Application of PCT/US2012/043914, filed on Jun. 24, 2012, and entitled "LIGHT CHAIN IMMUNOGLOBULIN FUSION PROTEINS AND METHODS OF USE THEREOF," which claims priority under 35 U.S.C. § 119(e) to U.S. Provisional Application Ser. No. 61/501,161, filed Jun. 24, 2011, entitled "LIGHT CHAIN IMMUNOGLOBULIN FUSION PROTEINS AND METHODS OF USE THEREOF", which is herein incorporated by reference in its entirety.

FIELD OF THE INVENTION

The invention relates to therapeutic antibodies and antibody fusion proteins, and methods for their preparation and use.

BACKGROUND OF THE INVENTION

Immunocytokines (antibody-cytokine fusion proteins) were first reported in the literature in the early 1990s and consisted of whole antibody fusions with cytokines such as lymphotoxin (TNF-β) or interleukin 2 (IL2). Subsequent studies in GD2-expressing tumor models in mice indicated that the ch14.18 antibody and ch14.18-IL2 immunocytokine both had anti-tumor activity but that the immunocytokine was far more potent than the antibody, even when combined with free IL2. Sabzevari H et al. (1994) *Proc Natl Acad Sci USA* 91:9626-30; Pancook J D et al. (1996) *Cancer Immunol Immunother* 42:88-92; Becker J C et al. (1996) *Proc Natl Acad Sci USA* 93:2702-7. In addition, immune-competent mice treated with the immunocytokine, but not the antibody plus IL2, developed an adaptive immune response dependent on CD8+ T cells that prevented subsequent tumor challenge. Becker J C et al. (1996) *J Exp Med* 183:2361-6; Becker J C et al. (1996) *Proc Natl Acad Sci USA* 93:7826-31. Thus, the targeting of IL2 to the tumor microenvironment induces an anti-tumor vaccine effect that is not possible with the antibody, either alone or together with the free cytokine. A related humanized immunocytokine, hu14.18-IL2, has recently achieved clinical proof of concept in relapsed neuroblastoma as monotherapy where it induced a significant number of complete responses in patients with no other treatment options. Many publications describe the ability of this molecule to activate several components of the immune system to kill tumor cells and to evoke a long lasting CD8 T cell memory response that resists subsequent tumor challenge.

SUMMARY OF THE INVENTION

In some embodiments, aspects of the invention relate to novel antibody fusion proteins that include a light chain fusion, wherein the amino terminus of the fusion protein is fused to the carboxy terminus of the light chain (e.g., the carboxy terminus of the light chain constant region). Surprisingly, fusions to the C-terminus of the light chain constant region do not disrupt natural effector functions of the intact antibody, despite the fact that the site of fusion is adjacent to interaction sites in the heavy chain required for these activities. For example, the ADCC (antibody-dependent cellular cytotoxicity) and CDC (complement-dependent cytotoxicity) effector functions are retained by antibodies containing light chain fusions, even when a fusion peptide is directly fused to the C-terminal Cys of a light chain constant region (e.g., of an IgG1 antibody).

In some embodiments, aspects of the invention relate to novel antibody fusion proteins that include a light chain fusion, wherein the carboxy terminus of the light chain is fused to the amino-terminus of second protein, and wherein the antibody binds to a cell-surface molecule (e.g., a cancer-associated cell surface antigen). In some embodiments, the fusion proteins are stabilized by the presence of a disulfide bond between the carboxy terminal Cys of the light chain constant region and the corresponding Cys of the heavy chain constant region. In some embodiments, binding of the antibody portion to a cell surface causes a conformational change in the fusion protein that reduces steric interference with the second protein, thereby uncovering its activity. Accordingly, a fusion protein described herein can be used to increase the cellular specificity of a protein by reducing its activity in the absence of binding to a target cell of interest (e.g., a cancer cell). This property can be useful to selectively mask or reduce the toxic properties of a fusion partner, thereby protecting non-target cells from the activity of a toxic fusion partner and only exposing target cells (e.g., cancer cells) to the toxic effects.

In some embodiments, a fusion protein described herein can be designed to selectively activate one or a subset of several (e.g., two) different receptor forms. For example, members of the IL2 family (e.g., IL2, IL21 or IL15) all can bind components of the IL2 intermediate receptor that they share. In some embodiments, a fusion of an IL2 family member to the C-terminus of an antibody light chain can be designed to sterically block one or more residues that activate the IL2 intermediate receptor (e.g., D20 on IL2 or a corresponding amino acid on another cytokine, for example IL21 or IL15). In some embodiments, the length of the N-terminal region of the cytokine can be altered (e.g., shortened or lengthened by 1, 2, 3, 4, 5, 6, 7, 8, 9, or 10 amino acids or more) to optimize the degree of selective inactivation by modifying the extent of steric hindrance of the activating amino acid(s) that are brought closer to the fusion junction due to the amino acid deletion. It should be appreciated that one of ordinary skill can readily make several different deletion forms and evaluate their relative activities against different receptors (e.g., as described herein). It should be appreciated that an optimal level of activity may depend on the intended use of the fusion protein. In some embodiments, the activity against a first receptor form may be reduced relative to the activity against a second receptor form. In some embodiments, the activity against the second receptor form also may be reduced.

In some embodiments, for cytokines that activate only one receptor form, a fusion protein as described herein can be designed to have a reduced level of receptor activation. In some embodiments, changes can be made to the number of amino acids between the C-terminus of the light chain and an amino acid on the cytokine that interacts with and activates the cytokine receptor. For example, the length of the N-terminal region of the cytokine fusion portion can be altered (e.g., shortened or lengthened by 1, 2, 3, 4, 5, 6, 7, 8, 9, or 10 amino acids or more). It should be appreciated that one of ordinary skill can readily make several different deletion forms and evaluate their relative activity in an appropriate in vivo or in vitro receptor assay. It should be appreciated that an optimal level of activity may depend on the intended use of the fusion protein. In some embodiments, the cytokine activity against a target receptor may be reduced. However, the lowest level of activity may not be optimal depending on the intended use. In some embodiments, the level of activity of the cytokine is not reduced by the fusion (or even may be increased).

Similarly, the activity of other proteins (e.g., other enzymes) fused to an antibody light chain (e.g., to an antibody that binds to a cell-surface receptor) can be altered (e.g., optimized for a particular use). In some embodiments, changes can be made to the number of amino acids between the C-terminus of the light chain and an amino acid on the protein that is important for activity. For example, the length of the N-terminal region of the cytokine fusion portion can be altered (e.g., shortened or lengthened by 1, 2, 3, 4, 5, 6, 7, 8, 9, or 10 amino acids or more). It should be appreciated that one of ordinary skill can readily make several different deletion forms and evaluate their relative activity in an appropriate in vivo or in vitro assay. It also should be appreciated that an optimal level of activity may depend on the intended use of the fusion protein. In some embodiments, the activity of the protein (e.g., enzyme) may be reduced. However, the lowest level of activity may not be optimal depending on the intended use. In some embodiments, the level of activity is not reduced by the fusion (or even may be increased).

In some embodiments, aspects of the invention relate to an immunoglobulin fusion protein comprising a first light chain fusion protein, wherein the first light chain fusion protein includes an immunoglobulin light chain constant region and a fusion peptide fused to the C-terminus of the immunoglobulin light chain constant region. In some embodiments, the fusion peptide is a non-immunoglobulin peptide. In some embodiments, the fusion peptide is an immunoglobulin that binds specifically to a cell surface antigen. In some embodiments, an N-terminal region of a cytokine is used as a linker to connect the C-terminus of the immunoglobulin light chain constant region to the N-terminus of the fusion peptide. In some embodiments, the immunoglobulin also includes a first immunoglobulin heavy chain protein (e.g., a first antibody heavy chain or a portion thereof).

In some embodiments, the fusion peptide is between 5 and 500 amino acids long. In some embodiments, the fusion peptide comprises an alpha helical bundle. In some embodiments, the fusion peptide is a receptor-binding protein. It should be appreciated that the non-immunoglobulin peptide can be a cytokine as described herein. In some embodiments, the cytokine is IL-2, IL-7, IL-15, IL-21, GM-CSF, or α-interferon. However, other cytokines can be fused to the C-terminus of the light chain as the invention is not limited in this respect. In some embodiments, the fusion peptide is a protein enzyme or ribonuclease. In some embodiments, the fusion peptide is a single chain Fv and an N-terminal cytokine peptide is used as a linker to connect the C-terminus of the immunoglobulin light chain constant region to the N-terminus of the single chain Fv. In some embodiments, the N-terminal cytokine peptide is an IL2 N-terminal peptide. In some embodiments, the N-terminal cytokine peptide is 1-10 amino acids long.

In some embodiments, the immunoglobulin fusion protein also includes a variable region (e.g., a full length variable region or an antigen-binding portion thereof) fused to the N-terminus of the light chain constant region, and/or a variable region (e.g., a full length variable region or an antigen-binding portion thereof) at the N-terminus of a heavy chain constant region.

In some embodiments, the light chain constant region is a $C_\kappa$ or $C_\lambda$ constant region. In some embodiments, the heavy chain is an Ig G heavy chain. In some embodiments, the Ig G heavy chain is an Ig G1 heavy chain, an Ig G3 heavy chain, an Ig G2 or Ig G4 heavy chain. In some embodiments, the Ig G2 or Ig G4 heavy chain is modified to include an Ig G1 or Ig G3 sequence that confers ADCC and/or CDC effector function. In some embodiments, the Ig G1 sequence that confers ADCC and/or CDC effector function is an Ig G1 hinge.

In some embodiments, the fusion peptide is fused to the C-terminus of the immunoglobulin light chain constant region without a linker peptide. In some embodiments, the fusion peptide is fused to the C-terminal Cys of the immunoglobulin light chain constant region. In some embodiments, the fusion peptide is fused to the C-terminus of the immunoglobulin light chain constant region via a linker peptide. It should be appreciated that the linker peptide can be of any suitable length, for example, 1-20 amino acids long, or about 5 amino acids long. In some embodiments, the linker peptide is a poly-Gly peptide, a (Gly4-Ser)x combination peptide, or 3-10 amino acids from the N-terminus of an IL2-like cytokine, or the first 7 N-terminal amino acids from IL2.

In some embodiments, each of the immunoglobulin peptides and fusion peptides are independently human, mouse, dog, bovine, or cat sequences. In some embodiments, one or more variable regions of the first heavy and light chains are murine sequences. It should be appreciated that the sequences can be humanized, chimeric, variant (e.g., one or more mutations may be present in any of the immunoglobulin regions), or any combination thereof.

In some embodiments, the fusion peptide comprises a human cytokine sequence. In some embodiments, the cytokine has a mutation at a residue that is a contact point with a receptor, an active site, or a combination thereof. In some embodiments, the mutation that reduces the cytokine activity. For example, the fusion peptide can be an IL2 having a mutation at one or more positions corresponding in human IL2 to D20, R38, N88, or Q126.

In some embodiments, the first heavy and light chains bind specifically to a cell surface antigen (e.g., a cancer associated antigen). Accordingly, in some embodiments, the first heavy and light chains bind specifically to a tumor antigen. In some embodiments, the tumor antigen is a nucleic acid, e.g., a DNA molecule. In some embodiments, the tumor antigen is not a nucleic acid. In some embodiments, the tumor antigen is a proteinaceous tumor antigen, for example, a polypeptide. In some embodiments, the tumor antigen is a polysaccharide. In some embodiments, the tumor antigen is GD2, CD20, CD19, CSPG, or EpCAM. In some embodiments, the immunoglobulin binds specifically to a viral protein. In some embodiments, the cell surface antigen and/or the tumor antigen is a viral protein. In some embodiments, the immunoglobulin (e.g., the first heavy and light chain immunoglobulin proteins bind to a target antigen with an affinity or Kd from about $10^{-7}$ to about $10^{-12}$ M. However, they may have higher or lower affinities as aspects of the invention are not limited in this respect.

In some embodiments, aspects of the invention relate to novel immunocytokines. Immunocytokines are genetically engineered antibodies linked to potent cytokines (e.g., IL2) in order to direct the cytokines to a disease site where they will be effective. Aspects of the invention relate to novel cytokines wherein the amino terminus of the cytokine is fused to the carboxy terminus of the antibody light chain (e.g., to the carboxy terminus of the light chain of an antibody that binds to a cell surface protein). Light chain fusions were found to retain both ADCC and CDC effector functions despite the presence of the cytokine attached to the C-terminal end of the light chain constant region. In addition, the pharmacokinetics of the light chain fusions were found to be better (e.g., longer half-life) than those of heavy chain fusions. These observations support novel uses for the light-chain fusion immunocytokines. In some embodiments, light-chain fusion immunocytokines can be delivered lymphatically (e.g., subcutaneously) and exhibit sufficient bioavailability to be clinically effective. In some embodiments, light-chain immunocytokines are useful to treat certain lymphatic cancers (e.g., lymphomas and leukemia), as well as cancers associated with lymphatic metastasis (e.g., certain breast cancers and other cancers where metastases to the lymphatics are common).

Similarly, in some embodiments, fusions of other proteins (e.g., therapeutic enzymes) to the C-terminus of an antibody light chain (e.g., the light chain of an antibody that binds to a cell surface protein) can be administered subcutaneously to treat a disease (e.g., cancer).

In some embodiments, the frequency of dosing may be reduced by administering light-chain fusion immunocytokines instead of heavy-chain fusion immunocytokines. In some embodiments, subcutaneous administration of light-chain fusion immunocytokines provides a reservoir or depot of bioavailable molecules that can enter the blood stream and provide therapeutic benefits over a longer period of time than possible with traditional heavy-chain immunocytokine fusions.

Accordingly, in some embodiments, a light chain antibody fusion protein (e.g., immunocytokine) may be administered subcutaneously at a dosage of less than about 50 mg per square meter to a subject. In some embodiments, a light chain antibody fusion protein (e.g., immunocytokine) may be administered intravenously at a dosage of less than about 10 mg per square meter (e.g., about 5-10 mg per square meter, about 1-5 mg per square meter, or less). However, it should be appreciated that higher doses also may be used in some embodiments. In some embodiments, the immunoglobulin fusion protein or composition is administered at a frequency of once per week or at a lower frequency (e.g., once every two weeks, once every three weeks, monthly). However, it should be appreciated that a fusion protein or composition described herein may be administered at any frequency, including daily, or once every 2, 3, 4, 5, or 6 days, in some embodiments.

Immunocytokines that include a fusion of the cytokine to the heavy chain of the antibody have previously been tested and shown to stimulate strong immune responses against tumors in mice, in some cases leading to tumor eradication and long-term protection against relapse. Examples, of heavy chain fusions include fusions with anti-GD2 binding antibody sequences (GD2 is an antigen associated with neuroblastomas and melanomas), anti-EpCAM binding antibody sequences (EpCAM is associated with prostate, lung, colon, breast and gastric cancers). However, heavy chain fusion proteins have required modifications to increase their half-life and therapeutic effectiveness. In contrast, light chain fusion proteins have significantly longer half-lives and increased bioavailability when compared to heavy-chain immunocytokines, while retaining both heavy chain ADCC and CDC effector functions and cytokine activity.

In some embodiments, aspects of the invention relate to an immunoglobulin fusion protein comprising a heavy chain and a light chain fusion protein, wherein the light chain fusion protein comprises an immunoglobulin light chain constant region and a fusion peptide, wherein the fusion peptide is fused to the C-terminus of the immunoglobulin light chain constant region. In some embodiments, the fusion peptide is a single chain Fv. In some embodiments, the fusion peptide is a non-immunoglobulin peptide. In some embodiments, the fusion peptide is between 5 and 500 amino acids long. In some embodiments, the fusion peptide comprises an alpha helical bundle. In some embodiments, the fusion peptide is a receptor-binding protein. In some embodiments, the fusion peptide is a cytokine. In some embodiments, the cytokine is IL-7, IL-15, IL-21, GM-CSF or α-interferon. In some embodiments, the cytokine is IL2.

It should be appreciated that the fusion peptide may be any suitable peptide fused to the C-terminus of the immunoglobulin light chain. In some embodiments, the fusion peptide is cyotoxic or cytostatic. In some embodiments, the fusion peptide provides a detectable signal. In some embodiments, the fusion peptide is protein enzyme or toxin such as a ribonuclease.

In some embodiments, the immunoglobulin fusion protein further comprises a variable region fused to the N-terminus of the light chain constant region. In some embodiments, the light chain constant region is a $C_\kappa$ or $C_\lambda$ constant region. In some embodiments, the heavy chain is an IgG heavy chain. In some embodiments, the IgG heavy chain is an IgG1 or IgG3 heavy chain. In some embodiments, the IgG heavy chain is an IgG2 or IgG4 heavy chain. In some embodiments, the IgG2 or IgG4 heavy chain is modified to include an IgG1 or IgG3 sequence (e.g., an IgG1 hinge) that confers ADCC and/or CDC effector function, or better physical properties.

In some embodiments, the heavy chain is an IgA, IgD, IgE, or IgM heavy chain.

In some embodiments, the fusion peptide is fused to the C-terminus of the immunoglobulin light chain constant region without a linker peptide. In some embodiments, the fusion peptide is fused to the C-terminal Cys of the immunoglobulin light chain constant region.

In some embodiments, the immunoglobulin contains a fusion peptide that is fused to the C-terminus of the immunoglobulin light chain constant region via a linker peptide. In some embodiments, the linker peptide is 1-20 amino acids long. In some embodiments, the linker peptide is about 5 amino acids long. In some embodiments, the linker peptide is a poly-Gly peptide or a (Gly4-Ser)x combination peptide. In some embodiments, the linker peptide has a sequence that corresponds to an amino-terminal peptide of a cytokine.

In some embodiments, one or more amino acid residues (e.g., 1-25, 1-20, 1-15, 1-10, 1-5, or other number) are removed from or added to the amino terminus of the fusion partner. According to aspects of the invention, the length and conformation of the connection between the light chain and the fusion partner impacts the activity or selectivity of the fusion protein. In some embodiments, a fusion partner can be highly active if the distance between the C-terminus of the light chain an active amino acid on the fusion partner (e.g., an amino acid that is important for receptor contact) is around 20 amino acids (e.g., ~23-24 residues). In some embodiments, the activity of the fusion partner can be reduced by removing one or more (e.g., 2, 3, 4, 5, 6, 7, 8, 9, or 10) amino acids from the N-terminal region of the fusion partner. It should be appreciated that the precise number of residues required to be deleted for inactivation may depend on the fusion partner. However, one of skill in the art can test different deletion lengths to identify ones that result in the desired level of inactivation.

In some embodiments, one or more activities that are reduced by fusion to the C-terminus of an antibody light chain can be recovered upon binding to an antibody target (e.g., on a cell surface) due to a conformational change of the antibody upon binding resulting in a reduction of the steric hindrance that inactivated the fusion partner.

In some embodiments, a bead binding assay can be used to evaluate the level of activity of a protein fusion partner (e.g., a cytokine) upon binding of the antibody partner to a target (e.g., a cell surface) relative to the activity of the fusion partner in solution (e.g., in the absence of antibody binding). It should be appreciated that a bead binding assay can be developed by coating a bead with a target antigen (e.g., a cell-surface protein, for example a cell-surface protein associated with cancer) that is selectively bound by the antibody portion of a fusion protein described herein. Any suitable bead size can be used. In some embodiments, the diameter of the bead is approximately the size of a target cell. However, a bead can be smaller or larger. It also should be appreciated that other solid substrates (e.g., planar surfaces, plates, gels, channel, chromatography material, etc., or any combination thereof) can be used (e.g., coated with a target antigen) instead of a bead in order to perform an assay to compare the activity of a fusion protein in solution relative to a substrate-bound fusion protein. This relative activity can be used to evaluate the likelihood that a fusion protein will be active when bound to a target cell (for example, even if the fusion protein is inactive or has low levels of activity in solution). In some embodiments, a relative increase in activity upon binding to an antigen-coated bead or other substrate as described herein is indicative that the fusion protein will have increased activity in vivo (e.g., when administered to a subject) when bound to a target antigen (e.g., a cell-surface antigen). In some embodiments, a relative increase in activity can be used to determine whether a fusion protein will display a selective increase in activity when administered to a subject (e.g., for a first receptor form relative to a second receptor form for fusion proteins that are capable of binding to and/or activating two or more different receptor forms, for example, high—intermediate—and/or low affinity receptors).

In some embodiments, several of the N-terminal amino acids (e.g., the first 3-20, e.g., the first 3, 4, 5, 6, 7, 8, 9, 10, or 10-20) of IL2 are inserted between the C terminal Cys of the L chain and the first residue of a fusion protein partner (e.g., cytokine, enzyme, scFv, or other protein) to help stabilize the fusion protein (e.g., by promoting the formation of disulfide bonds between the fused light chain and the heavy chain of the antibody). It should be appreciated that the number of IL2 amino acids that are useful to stabilize the fusion protein may depend on the fusion partners, but one of skill in the art can readily test different numbers and determine an appropriate number for a use of interest. In some embodiments, the insertion of N-terminal amino acids from IL2 can be used to produce a fusion protein that is activated (or for which activity is increased) upon binding to a target antigen (e.g., on a target cell). The number of IL2 residues that are useful to form a stable composition and/or a composition that is activated by antigen binding can be determined by one skilled in the art (e.g., using cell activation assays or bead binding assays as described herein). In some embodiments, several N-terminal amino acids (e.g., the first 3-20, e.g., the first 3, 4, 5, 6, 7, 8, 9, 10, or 10-20) from one or more other cytokines (e.g., other IL2 related cytokines) can be evaluated and/or used as a linker to stabilize a fusion construct and/or produce a fusion construct that is activated upon antigen binding.

In some embodiments, a light chain fusion protein has an amino acid sequence shown in one the following non-limiting sequences. In each of these sequences the light chain sequence is shown in upper case letters (with the variable region italicized) and the fusion peptide is shown in lower case letters. In these non-limiting embodiments, the light chain sequence contains a 14.18 mouse variable region, and a human light chain constant region fused to a human IL2 sequence. Non-limiting amino acid sequence variants are underlined of the IL2 sequence are underlined in lower case letters. A non-limiting 4 amino acid spacer is underlined in upper case letters for SEQ ID NOs: 3 and 4.

SEQ ID NO: 1

*EIVMTQSPATLSVSPGERATLSCRSSQSLVHRNGNTYLHWYLQKPGQSPKLLIH*

*KVSNRFSGVPDRFSGSGSGTDFTLKISRVEAEDLGVYFCSQSTHVPPLTFGAGTKLEL*

KRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGECa ptssstkktqlqlehllldlqmilnginnyknpkltrmltfkfympkkatelkhlqclee elkpleevlnlaqsknfhlrprdlisninvivlelkgsettfmceyadetativeflnrw itf<u>c</u>qsiistlt

SEQ ID NO: 2

*EIVMTQSPATLSVSPGERATLSCRSSQSLVHRNGNTYLHWYLQKPGQSPKLLIH*

*KVSNRFSGVPDRFSGSGSGTDFTLKISRVEAEDLGVYFCSQSTHVPPLTFGAGTKLEL*

KRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGECa ptssstkktqlqlehllldlqmilnginnyknpkltrmltfkfympkkatelkhlqclee elkpleevinlaqsknfhlrprdlisninvivlelkgsettfmceyadetativeflnrw itf<u>g</u>qsiistlt

SEQ ID NO: 3
EIVMTQSPATLSVSPGERATLSCRSSQSLVHRNGNTYLHWYLQKPGQSPKLLIH

KVSNRFSGVPDRFSGSGSGTDFTLKISRVEAEDLGVYFCSQSTHVPPLTFGAGTKLEL

KRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

QRVDaptssstkktqlqlehllldlqmilnginnyknpkltrmltfkfympkkatelkhl qcleeelkpleevlnlaqsknfhlrprdlisninvivlelkgsettfmceyadetative flnrwitf<u>c</u>qsiistlt

SEQ ID NO: 4
EIVMTQSPATLSVSPGERATLSCRSSQSLVHRNGNTYLHWYLQKPGQSPKLLIH

KVSNRFSGVPDRFSGSGSGTDFTLKISRVEAEDLGVYFCSQSTHVPPLTFGAGTKLEL

KRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

QRVDaptssstkktqlqlehllldlqmilnginnyknpkltrmltfkfympkkatelkhl qcleeelkpleevlnlaqsknfhlrprdlisninvivlelkgsettfmceyadetative flnrwitf<u>s</u>qsiistlt The sequence indicated by the lower case letters of SEQ ID NO: 1 corresponds to human IL2. The sequence corresponding to human IL2 is also set forth in SEQ ID NO: 13.
SEQ ID NO: 13
aptssstkktqlqlehllldlqmilnginnyknpkltrmltfkfympkkatelkhlqcleeelkpleevlnlaqsknfhlrprdlisni nvivlelkgsettfmceyadetativeflnrwitfcqsiistlt It should be appreciated that each of the immunoglobulin peptides and fusion peptides may independently be of any species origin (e.g., human, mouse, dog, bovine, cat, or other species sequences). It also should be appreciated that the sequences may be modified (e.g., humanized, and/or de-immunized, and/or to modify activity, etc.). In some embodiments, one or more variable regions are murine sequences. In some embodiments, one or more variable regions comprise humanized and/or de-immunized sequences. In some embodiments, the fusion peptide includes a human cytokine sequence. In some embodiments, an altered (e.g., mutated) sequence of one or more immunoglobulin regions is used, for example, to selectively reduce or enhance a specific effector function (e.g., a replacement of E233-L234-L235-G236 to P-V-A in human IgG1 for reduced ADCC; or a K322A mutation in human IgG1 for reduced CDC). It should be appreciated that sequence alterations may be single or multiple amino acid substitutions, insertions, deletions, duplications, or any combination thereof. It also should be appreciated that these or other sequence alterations may be used alone or in combination.

In some embodiments, the fusion peptide is a cytokine mutant (e.g., that has a mutation at a residue that is a contact point with a receptor, at a residue that reduces toxicity, and/or at a residue that alters specificity, etc., or any combination thereof), a cytokine fragment (e.g., that retains sufficient functional properties) or other cytokine variant, or any combination thereof. In some embodiments, a light chain antibody fusion may incorporate one or more cytokine (e.g., IL2) variants or fragments described in U.S. Pat. No. 7,371,371; 7,514,073; or 7,803,361 by Epstein et al., the disclosures of which are incorporated herein by reference. In some embodiments, a light chain antibody fusion may incorporate one or more cytokine (e.g., IL2, IL-4, IL-9) variants or fragments described in U.S. Pat. No. 6,028,176; 6,313,272; 6,335,426; 6,955,807; 7,105,653, or 7,423,123 by Shanafelt et al., the disclosures of which are incorporated herein by reference.

In some embodiments, the cytokine has a mutation that reduces the cytokine activity by a factor of from 5 to 100 fold.

In some embodiments, the cytokine is a human, mouse, canine, feline, bovine, or other species cytokine, or a variant thereof. In some embodiments, the cytokine is an IL2 having a mutation at one or more of positions corresponding in human IL2 to D20, R38, F42, N88 or Q126. In some embodiments, the cytokine is an IL-15 having a mutation at N72 (e.g., N72D).

In some embodiments, an immunoglobulin is fused to an agent, for example an imaging agent, a radio-labeled agent, a cytotoxic or cytostatic agent, etc., or any combination thereof via a fusion at the C-terminus of the light chain.

In some embodiments, the immunocytokine binds specifically to a tumor-associated antigen. In certain embodiments, the tumor-associated antigen is a nucleic acid. In certain embodiments, the tumor-associated antigen is a DNA molecule. In certain embodiments, the tumor-associated antigen is a proteinaceous tumor antigen. In certain embodiments, the tumor-associated antigen is a polysaccharide, a lipid, or a lipopolysaccharide. In certain embodiments, the tumor antigen-associated is a polypeptide. In certain embodiments, the tumor-associated antigen is selected from GD2, CD20, CD19, CSPG4 and EpCAM. In some embodiments, the tumor-associated antigen is an extracellular matrix antigen such as oncofetal fibronectin. In some embodiments, the tumor-associated antigen is a vasculature-specific antigen. In some embodiments, the tumor-associated antigen is a macrophage-specific antigen.

In some embodiments, the cytokine is selected from the group consisting of: IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, G-CSF, GM-CSF, TGF-β, and IFN-α/β. In some embodiments, the cytokine (e.g., human, non-human, mammalian, and/or recombinant) is a cytokine that induces production and/or activation of natural killer cells. In some embodiments, the cytokine (e.g., human, non-human, mammalian, and/or recombinant) is a cytokine that induces production and/or activation of cytotoxic T-cells.

According to some aspects of the invention, methods are provided for producing an immunoglobulin having a light chain fusion protein. In some embodiments, the N-terminus of the fusion peptide is fused directly to the C-terminus of the immunoglobulin light chain.

In some embodiments, a mutated version of the immunoglobulin gamma heavy chain constant region is provided. In some embodiments, a mutated version of a cytokine is provided. In some embodiments, the function of the cytokine is modified to maintain a balance between the cytokine activities and the effector function activities of the immunocytokine. In some embodiments, one or more mutant sequences may be used to reduce the activity of the cytokine and/or increase the activity of one or more immunoglobulin effector functions (e.g., to reduce the ratio of cytokine activity to effector function activity by a factor of 1-100 (e.g., 1-10, 10-20, 20-30, 30-40, 40-50, 50-60, 60-70, 70-80, 80-90, 90-100) relative to the ratio of activities using non-mutant sequences in the fusion protein).

According to other aspects of the invention, methods are provided for targeting a cytokine in a subject (e.g., a human or mammal). In some embodiments, the targeting methods comprise administering any one of the immunocytokines disclosed herein to the subject.

According to other aspects of the invention, methods are provided for promoting ADCC in a subject. In some embodiments, the methods for promoting ADCC comprise administering any one of the immunocytokines disclosed herein to the subject.

According to some aspects of the invention, methods are provided for providing immunocytokines with reduced immunogenicity based on differences when compared to immunocytokines in which the cytokine is fused to the heavy chain. These differences include the inherent lack of the light chain C-terminus to contribute energy of binding to human MHC class II molecules of possible fusion peptides that could be processed in vivo and presented by these molecules to helper T cells, and the reduced degradation of light chain fused immunocytokines after binding to Fc receptors on antigen presenting cells that could lead to their uptake and presentation.

In some embodiments, recombinant antibodies are immunocytokines and include one or more cytokine proteins or portions thereof. Immunocytokines of the invention generally include an antibody, or an antigen binding fragment or derivative thereof, that is capable of binding specifically to a target antigen, linked to a cytokine. Immunocytokines of the invention may include one or more peptide sequences that are suitable for administration to a particular subject (e.g., human, non-human, or non-rodent animal, e.g., dog, cat, etc.).

In some embodiments an antibody or an immunocytokine is a recombinant protein that can be expressed from a recombinant gene (e.g., that includes coding sequences for the antigen binding and/or cytokine polypeptides fused in frame in the appropriate configuration and under suitable genetic control). Accordingly, embodiments of the invention relate to recombinant nucleic acids that encode an antibody or an immunocytokine. Other embodiments include host cells.

Some embodiments of the invention provide nucleic acids (e.g., isolated nucleic acids) that encode all or a portion of antibodies, antigen-binding domains, cytokines, and/or immunocytokines described herein. In some embodiments, the nucleic acid coding sequences (e.g., of an antibody region and/or a cytokine) are optimized for cloning and/or expression (e.g., in mammalian cells). In some embodiments the nucleic acids are included in vectors (e.g., plasmids) having one or more replication and/or selectable sequences (e.g., origins of replication, antibiotic markers, etc.). Some embodiments of the invention provide host cells transformed with one or more nucleic acids of the invention.

In some embodiments, the host cell is a bacterial, yeast, insect, or mammalian cell. In some embodiments, the host cell is a CHO cell or an NS/0 cell.

In some embodiments, an immunoglobulin fusion protein (e.g., an immunocytokine) is provided that can be bound to and eluted from protein A Sepharose (e.g., using acidic conditions) and remain biologically active and in a non-aggregated state. In some embodiments, an immunoglobulin fusion protein (e.g., an immunocytokine) can be isolated by contacting a host cell extract described herein to a suitable column (e.g., a protein A column) and eluting bound protein (e.g., after one or more washing steps).

In some embodiments an immunocytokine is a synthetic protein that is produced using synthetic chemistry techniques.

It should be appreciated that regardless of how an immunocytokine is produced, the different portions of the protein (e.g., the cytokine, the antibody or antigen binding portion, and/or regions thereof) may be fused via one or more linker peptides. In the case of recombinant fusion proteins, the linkers are encoded by nucleic acid sequences that are located, in frame, in between the coding regions for the different immunocytokine portions. In the case of synthetic proteins, the linker peptides are introduced during synthesis. In some embodiments synthetic immunocytokines may include non-peptide linkers that connect the different portions of the protein.

In some embodiments, pharmaceutical compositions are provided. In some embodiments, the pharmaceutical compositions comprise (i) a therapeutically effective amount of any of one the immunoglobulins (e.g., immunocytokines) disclosed herein and (ii) a pharmaceutically acceptable carrier.

In some embodiments, a method of treating cancer (or assisting in the treatment of cancer) in a subject is provided. In some embodiments, a method includes administering an immunoglobulin fusion protein described herein (e.g., an immunocytokine) to a subject having a cancer, wherein the immunoglobulin fusion protein binds specifically to a tumor-associated antigen. In some embodiments, the tumor-associated antigen is expressed on the extracellular surface of a tumor cell of the cancer. In some embodiments, a method also includes determining that the tumor-associated antigen is expressed on the extracellular surface of a tumor cell of the cancer. In some embodiments, the tumor-associated antigen is an extracellular matrix antigen, a vasculature-specific antigen, or a macrophage-specific antigen.

In some embodiments, the immunoglobulin fusion protein is an immunocytokine and the cytokine fusion peptide induces NK cells, or cytotoxic T lymphocytes.

In some embodiments, a cancer being treated is lung cancer, breast cancer, prostate cancer, melanoma, osteosarcoma, neuroblastoma, or any other cancer (e.g., a cancer for which a cancer-specific antigen can be identified and the antibody portion of the antibody fusion protein can be targeted to).

In some embodiments, a method of promoting ADCC in a subject is provided, by administering an immunoglobulin fusion protein (e.g., an immunocytokine) described herein to a subject. In some embodiments, method for potentiating a cell-directed immune response in a subject is provided, by administering an immunoglobulin fusion protein (e.g., an immunocytokine) described herein to a subject, wherein the immunoglobulin fusion protein binds specifically to an antigen that is expressed on the extracellular surface of a cell in the subject. In some embodiments, the cell is a tumor cell and the antigen is tumor antigen. In some embodiments, a second anti-cancer compound also is administered (e.g., simultaneously, concurrently, before, and/or after an immunoglobulin treatment regimen). In some embodiments, the second anti-cancer compound is a chemotherapeutic agent. In some embodiments, the subject is further treated (e.g., concurrently, before, and/or after) with radiation. In some embodiments, the immunoglobulin fusion protein or composition is administered subcutaneously. In some embodiments, the immunoglobulin fusion protein or composition is administered subcutaneously at a dosage of less than 50 mg per square meter. In some embodiments, the immunoglobulin fusion protein or composition is administered at a frequency of once per week, once every two weeks, or less frequently.

Accordingly, in some embodiments, methods for potentiating a cell-directed immune response in a subject are provided using an immunocytokine described herein. In some embodiments, the methods comprise administering a pharmaceutical composition comprising a therapeutically effective amount of any one of the immunocytokines disclosed herein and a pharmaceutically acceptable carrier. In some embodiments, the immunocytokine binds specifically to an antigen that is expressed on the extracellular surface of a cell. In some embodiments, the cell is a tumor cell and the antigen is a tumor antigen. In some embodiments, the cell is a B-cell and the antigen is a B-cell antigen (e.g., CD20 or other suitable antigen). In some aspects of the invention methods for treating cancer in a subject are provided. In some embodiments, the methods comprise: administering a pharmaceutical composition comprising a therapeutically effective amount of any one of the immunocytokines disclosed herein and a pharmaceutically acceptable carrier, wherein the immunocytokine binds specifically to a tumor antigen that is expressed on the extracellular surface of a tumor cell of the cancer. In some embodiments, the methods comprise determining that a tumor antigen is expressed on the extracellular surface of a tumor cell of the cancer; and administering a pharmaceutical composition comprising a therapeutically effective amount of any one of the immunocytokines disclosed herein and a pharmaceutically acceptable carrier, wherein the immunocytokine binds specifically to the tumor antigen. In some embodiments, the methods further comprise administering an anti-cancer compound other than the immunocytokine in combination with the pharmaceutical composition. In some embodiments, the methods further comprise subjecting the subject to one or more additional therapies, for example, but not limited to, prior or concurrent chemotherapy, tumor surgery, local radiation, radiofrequency ablation or other temperature based local tumor therapy. In certain embodiments, the additional therapy is given after one or more courses of immunocytokine therapy.

In some embodiments, a subject being treated has a cancer selected from the group consisting of lung cancer, breast cancer, prostate cancer, colon cancer, gastric cancer, liver cancer, pancreatic cancer, head and neck cancer, thyroid cancer, lymphoma, leukemia, multiple myeloma, melanoma, sarcoma, and neuroblastoma. However, it should be appreciated that other cancers or tumors may be treated as described herein.

In some embodiments, an immunoglobulin fusion protein described herein includes an antibody portion wherein the light chain is fused to an imaging agent, a cytotoxic agent, or a cytostatic agent.

These and other aspects of the invention are further illustrated by the following description and examples.

DETAILED DESCRIPTION OF THE INVENTION

In some embodiments, aspects of the present invention provide novel antibody fusion proteins useful for targeting fusion peptides to specific tissues in subjects. Embodiments of the invention are useful for targeting diseased cells (e.g., cancer cells) in human and non-human animals. Antibodies of the invention may be fused to cytokines (e.g., to form immunocytokines for therapeutic applications), imaging molecules (e.g., for targeted imaging applications), and/or radiolabeled molecules (e.g., for targeted radiotherapy). It should be appreciated that in some embodiments immunocytokines also may be radiolabeled as aspects of the invention are not limited in this respect.

Figure 1:
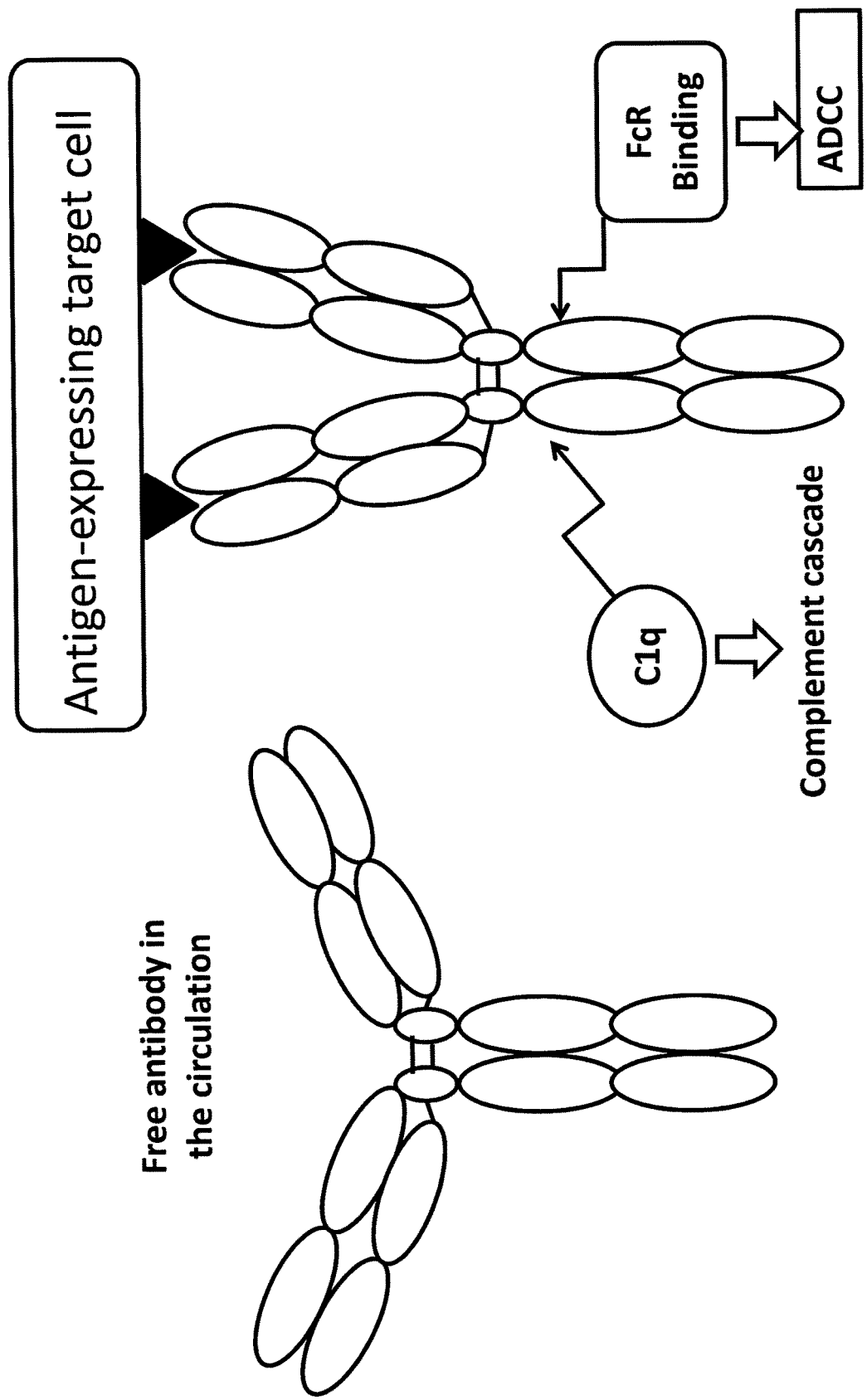
FIG. 1 is a non-limiting illustration of an antibody and structural changes that occur upon binding to an antigen-expressing target cell.
Figure 2:
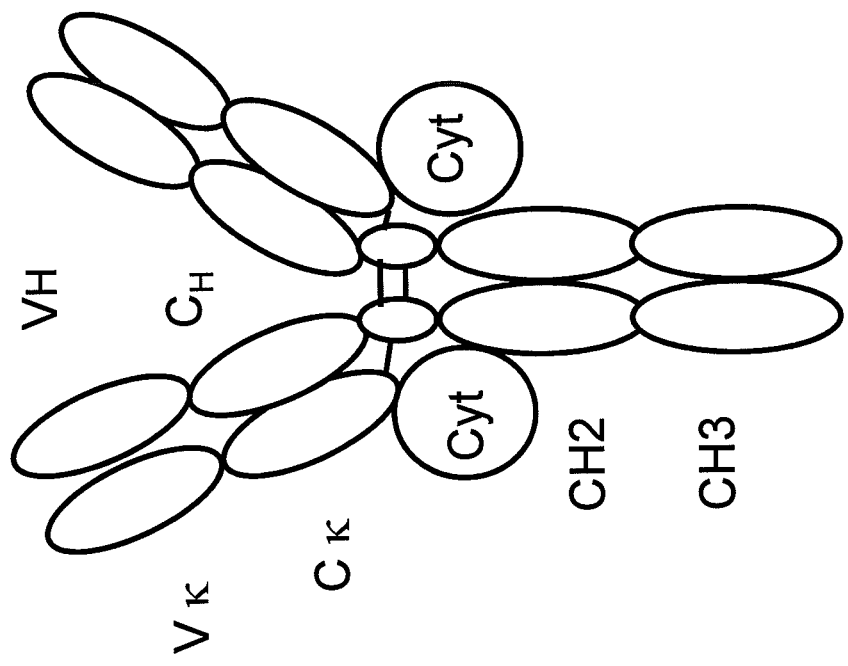
FIG. 2 illustrates non-limiting embodiments of a cytokine fused to the C-terminus of an antibody heavy chain (left panel) and a cytokine fused the C-terminus of an antibody light chain (right panel)
Figure 2:
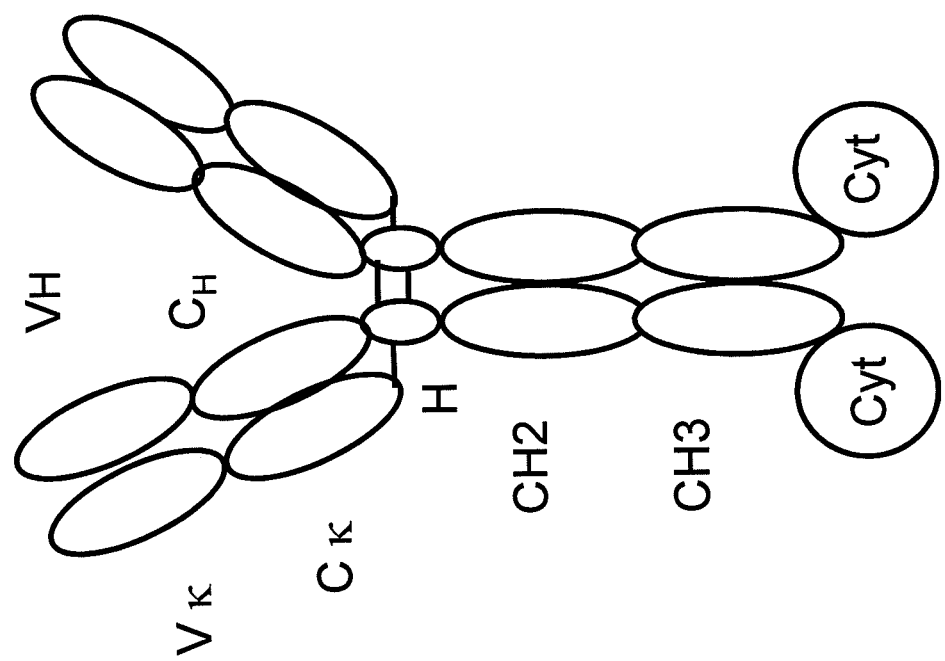

Aspects of the invention are based, at least in part, on the unexpected properties of antibodies having a light chain fused, via the C-terminus, to the N-terminus of a fusion peptide (e.g., a cytokine or other fusion peptide). In some embodiments, C-terminal fusions to the light chain of an antibody (see, for example, FIG. 2) do not disrupt the effector functions (e.g., the ADCC and CDC functions of an IgG1 antibody) or the function of the fusion peptide (e.g., cytokine). In addition, antibodies having a C-terminal fusion on the light chain demonstrate increased serum half-life and subcutaneous bioavailability. Accordingly, antibodies having a C-terminal fusion on the light chain can be used to deliver a fusion peptide (e.g., a cytokine) more effectively and at lower dosages than antibodies having a C-terminal fusion on the heavy chain.

In some embodiments, immunocytokines comprising an antibody having a cytokine fused to the C-terminus of the light chain have improved clinical properties relative to immunocytokines comprising an antibody having a cytokine fused to the C-terminus of the heavy chain. Immunocytokines comprising a cytokine fused to the heavy chain of the antibody exhibit normal antigen binding and normal ADCC. However, the C-terminal fusion alters the structure of the Fc region, even when a flexible peptide linker is used. As a result, immunocytokines having a heavy chain fusion exhibit low complement killing (CDC) relative to intact antibodies. In addition, heavy chain immunocytokine fusions are characterized by high Fc receptor (FcR) binding in the absence of antigen binding. This results in a relatively short half-life. These properties of heavy chain immunocytokine fusions can be altered, for example, to reduce or eliminate FcR binding by deglycosylating the immunocytokine and/or to prevent intracellular proteolysis by modifying the linker. However, deglycosylation results in loss of ADCC and CDC, and linker modified constructs still have relatively low CDC and sub-optimal pharmacokinetic properties.

In contrast, immunocytokines having a light chain fusion retain the functions of the intact antibody and the cytokine, even without a linker peptide. For example, light chain immunocytokine fusions exhibit normal antigen binding, ADCC, cytokine activity, improved CDC and reduced clearance by FcR receptor bearing cells. In some embodiments, without wishing to be bound by theory, light chain fusions avoid heavy chain distortions, and this results in decreased degradation after uptake by FcR bearing cells, followed by recycling out of the cell.

In some embodiments, light chain immunocytokine fusions are based on IgG (e.g., IgG1 or IgG3) antibodies. An IgG antibody is a tetramer that includes two heavy chains and two light chains, each heavy chain being linked to the other heavy chain and also to one light chain. Each heavy chain includes an N-terminal variable ($V_H$) region linked to a C-terminal constant ($C_H$) region. The two heavy chains are linked to each other through one or more disulfide bonds between the respective $C_H$ regions. Each light chain includes an N-terminal variable ($V_L$) region linked to a C-terminal constant ($C_L$) region. The light chain can be a kappa chain or a lambda chain, depending on its $V_L$ and $C_L$ regions. A kappa light chain includes a $V_\kappa$ and a $C_\kappa$ region, while a lambda light chain includes a $V_\lambda$ and $C_\lambda$ region. Each heavy chain is linked to one light chain through one or more disulfide bonds between the $C_H$ region and the $C_L$ (e.g., $C_\kappa$) region.

The $V_H$ and $V_L$ regions of an antibody determine the antigen specificity and affinity of the antibody. Together, the $C_H$ regions, in part, define the Fc portion of the antibody that is capable of directing effector functions antibody-dependent cellular cytotoxicity (ADCC) and/or complement-dependent cytotoxicity (CDC). It should be appreciated that in some embodiments a peptide is fused to the C-terminus of the light chain of a chimeric antibody. In some embodiments, in a chimeric antibody, the $V_H$ and $V_L$ regions of a first antibody (e.g., specific for a first antigen, and/or from a first species or antibody type) are substituted for the $V_H$ and $V_L$ regions of a second antibody (e.g., specific for a second antigen, and/or from a second species or antibody type), while retaining the Fc portion of the second antibody, resulting in an antibody with the antigen specificity (and other properties, e.g., immunogenicity, etc.) of the first antibody and the effector function characteristics of the second antibody.

It should be appreciated that any species of variable and constant regions may be used. In some embodiments, both heavy and light chains are human or humanized. In some embodiments, both variable and constant regions are human or humanized. In some embodiments antibodies can include a human, mouse, cow, dog, or cat heavy chain and a human, mouse, cow, dog, or cat light chain or a portion thereof (e.g., a kappa or lambda constant region). In some embodiments antibodies may be chimeric and include a variable region from a first species and a constant region from a second species. For example, antibodies may include a variable region from a mouse antibody (optionally humanized or canonized) fused to a constant region from a human antibody. Mouse variable regions have been identified for many different antigens. Since most mouse antibodies have kappa light chains, a mouse light chain variable region should generally be fused to a kappa constant region from a human antibody for optimal stability and performance of recombinant mouse/human antibodies. However, in some embodiments, a mouse variable region may be fused to a lambda constant region.

In some embodiments immunocytokines include a light chain having a variable region (e.g., a mouse variable region, a dog variable region, a humanized variable region, or any other suitable variable region) fused to a constant region (e.g., full length, or containing one or more point mutations and/or deletions) fused to a cytokine or a portion thereof. The recombinant light chain can be combined with a heavy chain (e.g., a recombinant heavy chain). The recombinant light chain may be either a lambda or a kappa light chain constant region. In some embodiments, when the variable region is a kappa variable region, a kappa constant region may be selected (even though a lambda constant region could be used in some embodiments).

In some embodiments, immunocytokines are provided that bind specifically to tumor-associated antigens. As used herein, the term "tumor-associated antigen" refers to a substance produced directly or indirectly by a tumor cell that induces a specific immune response in a host to the substance. Typically, the tumor antigen is expressed on the extracellular surface of a tumor cell. In some embodiments, the tumor antigen is a human antigen, a non-human homologue of a human tumor-associated antigen, or any other non-human tumor-associated antigen. In some embodiments, the tumor antigen is GD2-ganglioside, CD19, CD20, EPCAM, or CSPG4. Other suitable tumor antigens include, for example, p185 HER2/neu (erb-B1; Pisk et al., J. Exp. Med., 181:2109-2117 (1995)); epidermal growth factor receptor (EGFR) (Harris et al., Breast Cancer Res. Treat, 29:

1-2 (1994)); carcinoembryonic antigens (CEA) (Kwong et al., J. Natl. Cancer Inst., 85:982-990 (1995); carcinoma-associated mutated mucins (MUC-1 gene products; Jerome et al., J. Immunol., 151:1654-1662 (1993)); E7 and E6 proteins of human papillomavirus (Ressing et al., J. Immunol, 154:5934-5943 (1995)); prostate specific membrane antigen (PSMA Israeh, et al., Cancer Res., 54:1807-1811 (1994)); and idiotypic epitopes or antigens, for example, immunoglobulin idiotypes or T cell receptor idiotypes (Chen et al., J. Immunol., 153: 4775-4787 (1994)).

However, it should be appreciated that the invention is not limited to immunocytokines that bind tumor antigens. For example, autoimmune diseases (e.g., Rheumatoid Arthritis, Multiple Sclerosis, Crohn's Disease, Psoriasis, etc.) may be treated using immunocytokines that bind specifically to a cell surface antigen of a cell that mediates an autoimmune response (e.g., a CD20 antigen, alpha-4 (α4) integrin, CD11a, etc.).

In certain embodiments, immunocytokines targeting one or more viral antigens on the surface of actively or latently infected cells are provided for the treatment of persistent viral infections such as HIV/AIDS. For example, the HIV viral reservoir may be treated with an immunocytokine targeting a conserved epitope in the membrane-bound HIV gp41 protein thereby leading to the destruction of latently infected cells expressing this antigen. Likewise, similar viral proteins expressed on the surface of other virally infected cells (e.g., cells infected with the hepatitis virus) may be targeted with an immunocytokine specifically binding such an antigen.

As used herein, the term "binds specifically" means that the immunocytokine or recombinant antibody is capable of specific binding to its target antigen in the presence of the antigen under suitable binding conditions known to one of skill in the art. In some embodiments, the immunocytokine or recombinant antibody has an affinity constant, $K_a$, in a range of $10^7$ $M^{-1}$ to $10^8$ $M^{-1}$, $10^8$ $M^{-1}$ to $10^9$ $M^{-1}$, $10^9$ $M^{-1}$ to $10^{10}$ $M^{-1}$, $10^{10}$ $M^{-1}$ to $10^{11}$ $M^{-1}$, or $10^{11}$ $M^{-1}$ to $10^{12}$ $M^{-1}$. In some embodiments, the immunocytokine or recombinant antibody has an affinity constant, $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, or at least $10^{12}$ $M^{-1}$.

In some embodiments, "binds specifically" means that at least 90 percent, at least 95 percent, at least 98 percent, or at least 99 percent, of antibody-antigen immune complexes formed when the antibody is contacted with a source of antigens, under conditions suitable for the formation of immune complexes, include a specified antigen. For example, the immunocytokine of the invention is said to bind specifically to GD2 when at least 90 percent of antibody-antigen immune complexes formed when the antibody-containing immunocytokine is contacted with a source of antigens, under conditions suitable for the formation of immune complexes, include GD2.

In some embodiments, immunocytokines of the invention may be used for veterinary applications. For example, light chain immunocytokine fusion proteins can be provided for killing antigen-expressing malignant cells in dogs, cats, or other non-human animals. Immunocytokines of the invention can be used in non-human animals in order to characterize their clinical efficacy in vivo. Preclinical data obtained from such studies are useful for the development of therapeutic agents for use in veterinary medicine, as well as further development and use of immunocytokines in human subjects in some embodiments.

In some embodiments, antibodies containing light chain variable and constant regions derived from different species (e.g., a variable region from mouse, whether humanized or not, and a constant region from dog) are more stable and/or have higher performance characteristics when the variable and constant regions are of the same isotype (e.g., matched to both be either kappa or lambda). Mouse antibody light chains are typically kappa light chains, whereas dog antibody light chains are typically lambda light chains. Accordingly, in some embodiments a mouse variable region (e.g., a mouse kappa variable region) is fused to a dog kappa constant region.

In some embodiments, the C-terminal amino acid of at least one light chain of an antibody is covalently linked to N-terminal amino acid of a fusion peptide (e.g., a cytokine). In some embodiments, the C-terminal amino acid of both light chains of an antibody are covalently linked to the N-terminal amino acid of a fusion peptide (e.g., a cytokine). In some embodiments, the C-terminal amino acid of one or both light chains of an antibody are genetically linked to the N-terminal amino acid of a fusion peptide (e.g., a cytokine).

It should be appreciated that the light chain, heavy chain, and cytokine portions of the immunocytokines can be connected with or without an intervening linker (e.g., peptide linker).

In some embodiments, a substitution or deletion of the C-terminal Cys residue on a light chain constant region results in a non-functional or poorly functional protein (e.g., due to the absence of the corresponding Cys-Cys bond between the heavy and light chain). Accordingly, in some embodiments, an immunocytokine having a C-terminal light chain fusion retains the C-terminal Cys of the light chain constant region.

Figure 3:
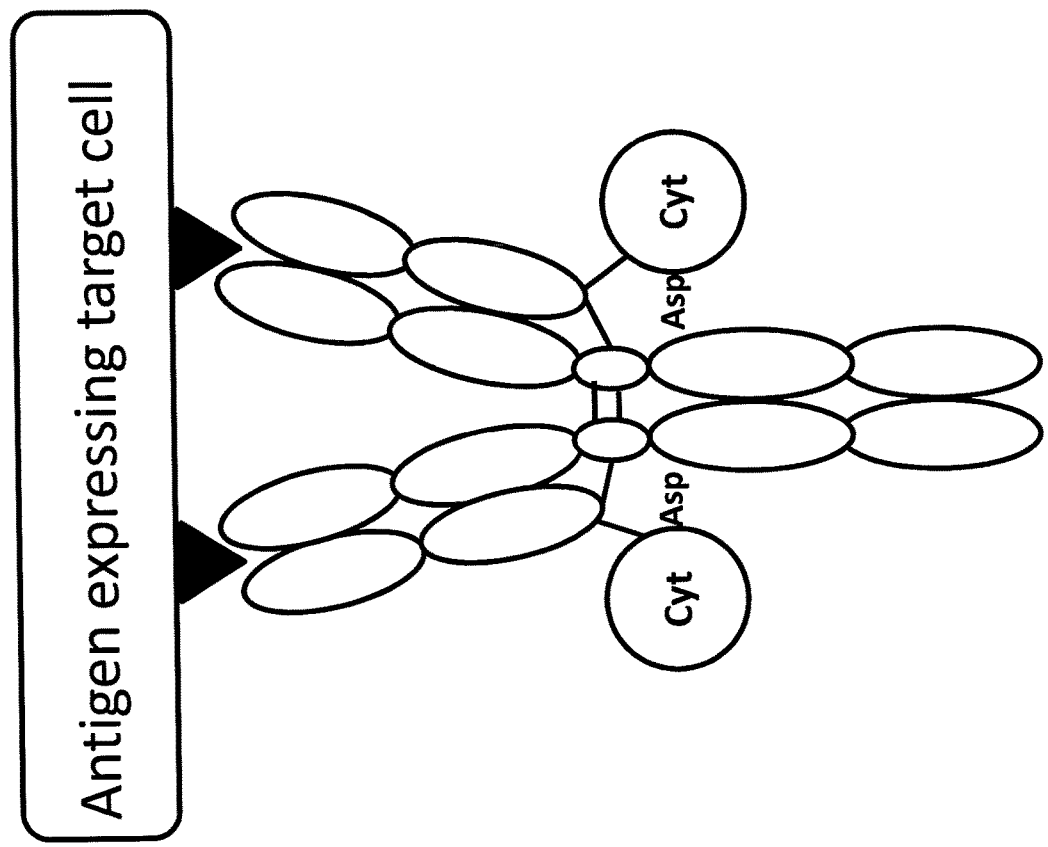
FIG. 3 is a non-limiting illustration of an immunocytokine having IL2 fused to the C-terminus of the light chain and the structural changes that occur upon binding to an antigen-expressing target cell.
Figure 3:
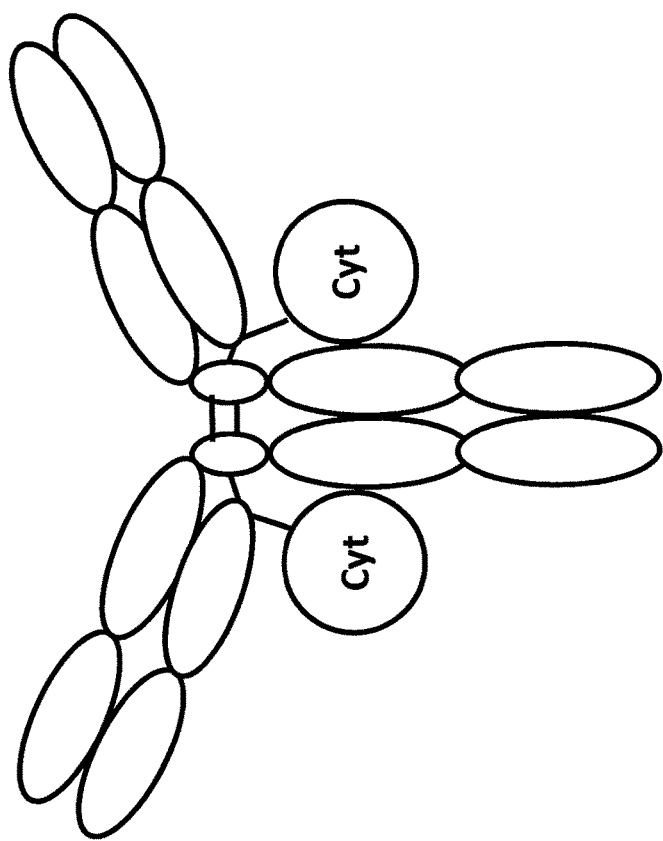
Figure 4:
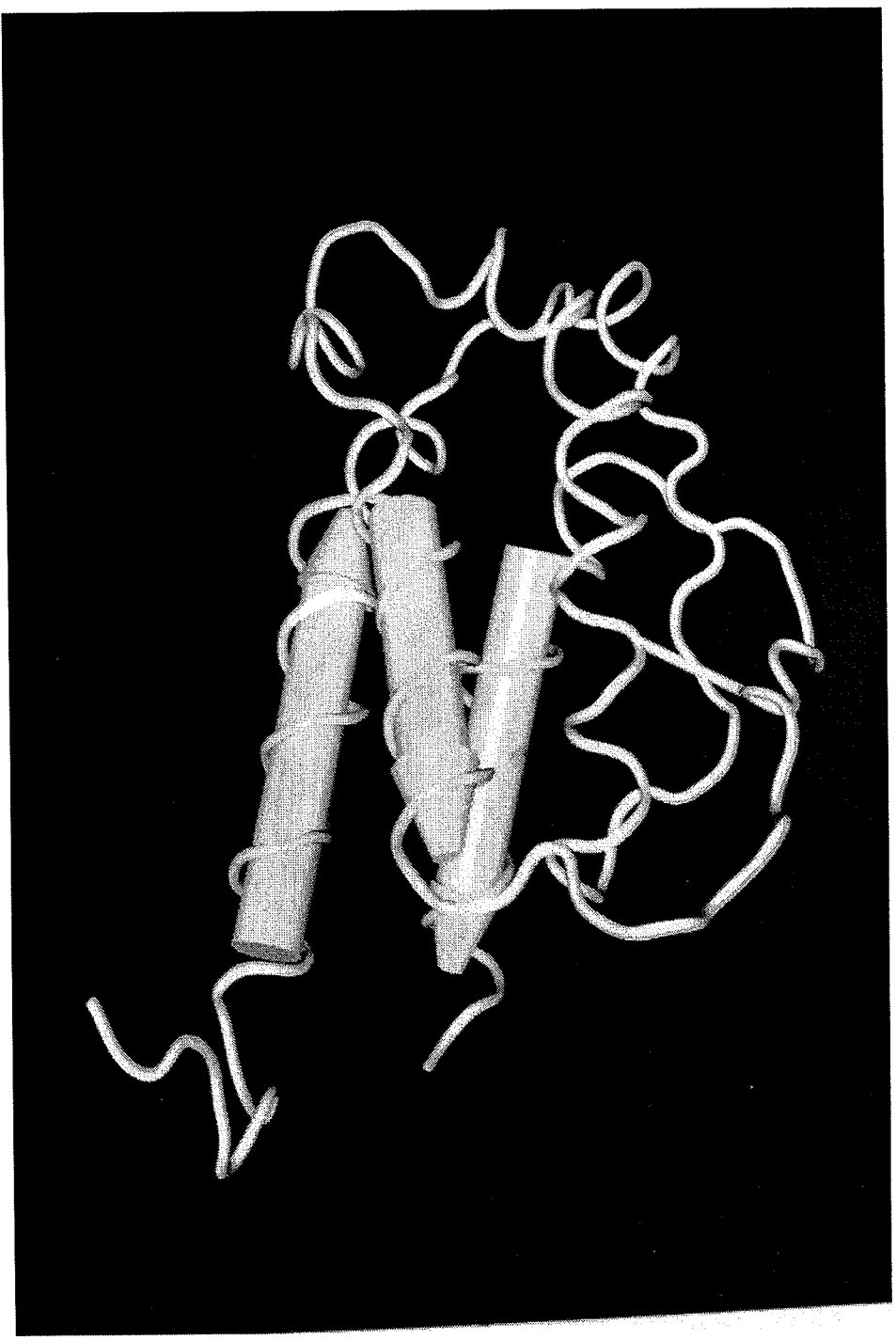
FIG. 4 illustrates a non-limiting embodiment of an IL2 protein showing the location of D20.

A non-limiting schematic representation of an embodiment of an immunocytokine of the invention is shown in FIG. 3. As illustrated in FIG. 3, a structural change occurs in the antibody upon binding to a cell that expresses a target antigen. In some embodiments, this structural change can unmask the fusion protein (e.g., cytokine) thereby increasing its activity. In solution, antibodies have a shape in which C-terminus of each light chain constant region is forced into the cleft at the hinge region of the heavy chain. Once the antibody binds to a multimeric antigen (e.g., on a cell surface) the Fab arms move into a configuration that exposes the hinge region for interaction with other proteins. In some embodiments, this configurational change can be used to expose a fusion peptide, for example a cytokine, or a portion thereof (for example a receptor binding region, active site, or other functional region) that is fused to the C-terminus of the light chain. Accordingly, in some embodiments, cytokine specificity can be further enhanced by creating light chain immunocytokine fusions wherein the cytokine is inactive, or relatively inactive in the absence of binding to a target cell (e.g., the activity is masked by the folding of the antibody portion of the immunocytokine), and wherein cytokine activity is increased upon antigen binding (e.g., binding to an antigen on a cell surface).

In some embodiments, mutant or altered cytokines with reduced activity may be used, for example, in a construct that masks the cytokine activity in the absence of antigen binding.

In some embodiments, the masking effect may be increased by modifying a cytokine. For example, one or more (e.g., 1-5, 5-10, etc.) N-terminal amino acids of a cytokine may be deleted to produce an immunocytokine characterized by shielding or masking of the cytokine by the antibody portion in the absence of antigen binding. In some embodiments, this reduces the distance between the light chain C-terminal Cys bond to the H chain and the first alpha helix of the cytokine which generally contains a critical receptor binding contact residue (e.g., Asp20 in IL2 and analogous Asp residues in other related cytokines like IL-21 and IL15), thereby further restricting access to this site in the unbound but not in the bound configuration.

Certain embodiments of the invention relate to isolated proteins and nucleic acids that encode the proteins. As used herein, an isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polypeptide.

Also provided are vectors useful for expression of an immunocytokine of the invention. In one embodiment the expression vector is suitable for use in mammalian host cells. Mammalian expression vectors can include non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a poly-adenylation site, splice donor and acceptor sites, and transcriptional termination sequences. Commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. A nucleic acid molecule of the invention can be inserted into an appropriate expression vector using standard methods of molecular biology which need not be described in further detail here. The expression vector can include a promoter or promoter/enhancer element that is positioned upstream of the coding nucleic acid molecule that is inserted into the vector. Expression vectors can optionally include at least one coding region for a selection marker and/or gene amplification element, e.g., dihydrofolate reductase (DHFR).

For expression of an immunocytokine of the invention, a vector or vectors containing nucleic acid sequences encoding the various polypeptides of the immunocytokine can be introduced into a suitable host cell or population of host cells.

The vector or vectors can be introduced into a host cell or cells using any suitable method, including, for example, electroporation, biolistic delivery (e.g., using a gene gun), lipofection, calcium phosphate precipitation, microinjection, viral transduction, nucleofection, sonoporation, magnetofection, and heat shock. Such methods are well known by persons skilled in the art and need not be described here. Following introduction of the vector or vectors into the host cell or cells, the cell or cells are maintained under physiologically suitable conditions suitable for in vitro cell culture, for a period of time sufficient to permit the cell or cells to express the immunocytokine.

As used herein, a host cell is a eukaryotic cell. In some embodiments, the host cell is a mammalian cell. In certain embodiments, the host cell is a mammalian cell line. In some embodiments, the mammalian cell line is non-Ig-secreting myeloma such as NS/0 or Sp2/0-Ag14. In some embodiments, the mammalian cell line is HEK293. In certain embodiments, the mammalian cell line is a Chinese hamster ovary (CHO) line. These and other suitable host cells are available from American Type Culture Collection (ATCC) (Manassas, Va.).

In some embodiments, an immunocytokine is secreted into the culture medium by the cells containing the expression vector or vectors. Secreted expressed immunocytokine can be readily isolated from culture by centrifugation (to remove cells) followed by immunoaffinity separation, for example using protein A or protein G chromatography, and/or using specific antigens to which the immunocytokine binds. In some embodiments, the immunoaffinity separation can alternatively or in addition involve an anti-cytokine antibody, e.g., and anti-IL2 antibody, as the immunoaffinity reagent.

Also provided are compositions that include an immunocytokine of the invention. In one embodiment, the composition is a pharmaceutical composition that includes an immunocytokine of the invention and a pharmaceutically acceptable carrier.

The term "pharmaceutically-acceptable carrier" means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with other compounds, and with each other, in a manner such that there is no interaction which would substantially impair the desired pharmaceutical efficiency.

Immunocytokines of the invention can be used to treat cancers (e.g., GD2-expressing cancers) in humans, and non-human animals (e.g., dogs, cats, etc.). As used herein, "cancer" refers to an abnormal uncontrolled growth of cells in a subject. The term "cancer" as used herein can refer to solid tumors, primary as well as metastatic cancers, as well as hematogenous ("liquid") cancers. In some embodiments, antigen-expressing cancers are cancers that have detectable antigen (e.g., GD2) expressed on their cell surface. GD2-expressing cancers are generally cancers of neuroectodermal origin and specifically can include, without limitation, melanoma, neuroblastoma, osteosarcoma, and small cell lung cancer.

As used herein, "to treat" means to slow or halt the progression of, or to reduce or eliminate, a disease in a subject having the disease. A subject having a disease is a subject that has at least one objectively identifiable manifestation of the disease.

As used herein, an "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective therapeutic treatment regimen can be planned which does not cause substantial toxicity and yet is effective to treat the particular subject. The effective amount for any particular application can vary depending on such factors as the disease or condition being treated, the particular active agent being administered, the size of the subject, or the severity of the disease or condition. One of ordinary skill in the art can empirically determine the effective amount of a particular active agent and/or other therapeutic agent without necessitating undue experimentation. It is preferred generally that a maximum dose be used, that is, the highest safe dose according to some medical judgment, although this is not necessarily the case for immune-stimulating agents. Multiple doses per week may be contemplated to achieve appropriate systemic levels of compounds. Appropriate systemic levels can be determined by, for example, measurement of the subject's peak or sustained plasma level of the drug.

"Dose" and "dosage" are used interchangeably herein. Generally, dosing depends on the biology of the fusion molecule and its pharmacodynamic effects. For example, immunocytokines containing IL2 cause a short period of lymphopenia due to margination of IL2 receptor bearing cells out of the circulation, followed by a rebound lymphocytosis of cells that have greatly upregulated IL2 receptor and are capable of receptor-mediated clearance of additionally administered immunocytokine. Therefore, in some embodiments, an initial dosing is provided over a period of two or three consecutive days and then not again for several weeks (e.g., about two to three weeks). In some embodiments (e.g., for IL2 containing immunocytokines), doses of active compounds will be from about 0.05 mg per square meter to about 50 mg per square meter, depending on the route of administration. It is expected that intravenous doses that range from 0.05 to 10 mg per square meter per day, for one or several days, or alternatively once per week, will yield the desired results. Similarly, it is expected that subcutaneous doses in the range of 1 to 100 mg per square meter per day, for one or several per days, or alternatively once per week (or less frequently) will yield the desired results. In other embodiments, where the fused protein has different biological properties and lower vascular toxicity than IL2 (or where the activity of the fused protein, e.g., IL2, has been reduced) higher doses may be used. Dosage may be adjusted appropriately to achieve desired drug levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any immunocytokine described herein, the therapeutically effective amount can be initially determined from animal models. A therapeutically effective dose can also be determined from human data for immunocytokines which have been tested in humans and for compounds which are known to exhibit similar pharmacological activities, such as other related active agents. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

In some embodiments, the immunocytokine may be administered in combination with a therapeutic antibody. In some embodiments, the immunocytokine of the invention can be administered in conjunction with at least one other anti-cancer treatment agent or anti-cancer treatment modality to treat the cancer. As used herein, "in conjunction with" or "in combination with" refers to any suitable form of combination therapy, for example simultaneous, overlapping, and/or sequential treatments. Anti-cancer treatment agents (e.g., anti-cancer compounds) and anti-cancer treatment modalities other than treatment with an immunocytokine of the invention can include chemotherapy (including combination chemotherapy), radiation therapy, surgery, other immunotherapy (e.g., cancer vaccines), and any combination thereof. It can also include the addition of one or more targeted therapies that inhibit specific signaling pathways (e.g., sunitinib, imatinib, erlotinib, etc.), that reduce both tumor cell growth as well as tumor-induced immunosuppression. In some embodiments, the anti-cancer treatment is local radiation or radiofrequency ablation. Anti-cancer treatments such as cyclophosphamide, doxorubicin, valinomycin, hormone therapy, and other therapies disclosed herein or otherwise known in the art may be used.

As used herein, an "anti-cancer compound" refers to an agent which is administered to a subject for the purpose of treating a cancer. Anti-cancer compounds include, but are not limited to anti-proliferative compounds, anti-neoplastic compounds, anti-cancer supplementary potentiating agents and radioactive agents. One of ordinary skill in the art is familiar with a variety of anti-cancer compounds. Examples of anti-cancer compounds include, but are not limited to, the following: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Bendamustine; Bortezimib; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Revlimid; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride;

Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid, 2-chloro-2'-arabino-fluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone. Radioactive agents may also be used. Examples of radioactive agents include but are not limited to Fibrinogen I 125; Fludeoxyglucose F18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate-Hg 203; Merisoprol Hg 197; Selenomethionine Se 75; Technetium Tc 99m Atimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium 99m Lidofenin; Technetium Tc 99 mm Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Ic 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125: Thyroxine I 131; Tolpovidone I 131; Triolein I 125; Triolein I 131.

In some embodiments, an immunocytokine is administered in combination with a traditional chemotherapy protocol, for example one that activates the immune system and is not itself immunosuppressive (e.g., one or more taxanes, doxorubicin, etc., or any combination thereof), or that reduces tumor-induced immune suppression due to regulatory T cells (e.g., cyclophosphamide) or myeloid suppressor cells (e.g., gemcitabine).

For use in therapy, formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

For use in therapy, an effective amount of the immunocytokine can be administered to a subject by any mode that delivers the immunocytokine to the desired target tissue. Administering the pharmaceutical composition of the present invention may be accomplished by any means known to the skilled artisan. Routes of administration include but are not limited to intravenous and subcutaneous.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For subcutaneous administration, agents can be chosen that do not cause local skin irritation. In some embodiments, agents are generally isotonic and do not contain high levels of harsh detergents.

Alternatively, the active compounds may be in powder form for constitution with a suitable vehicle, e.g., sterile pyrogen-free water, before use.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Genetically Engineered Immunocytokines Having a Cytokine Fused to the C-Terminus of an Antibody Light Chain In some embodiments, an antibody against a therapeutic target is engineered to include a cytokine fused to the C-terminus of the antibody light chain.

For example, an antibody against GD2 is engineered to include IL2 fused to the C-terminus of the light chain. GD2 is a disialoganglioside expressed on tumors of neuroectodermal origin, including human neuroblastoma and melanoma, with highly restricted expression on normal tissues, principally to the cerebellum and peripheral nerves in humans. The relatively tumor-specific expression of GD2 makes it an attractive target for immunotherapy, for example with monoclonal antibodies. Melanomas, sarcomas, and neuroblastomas abundantly express GD2 on the cell surface where it is susceptible to immune attack by antibodies. Overexpression of GD2 on these tumors is striking, as is the frequency of clinical responses after treatment of neuroblastoma with monoclonal antibodies against GD2. Similar to other types of cancer, conventional approaches to treatment of various GD2-positive cancers include surgery, radiotherapy, and chemotherapy.

Antibodies, including monoclonal antibodies, have been developed for use in treating GD2-positive cancers. A murine monoclonal anti-human GD2 antibody, designated 14.18, was reported by Mujoo and colleagues in 1987. Mujoo K et al. (1987) *Cancer Res* 47:1098-104. With the advent of antibody engineering, chimeric and humanized forms of 14.18 were subsequently developed. Gillies S et al. (1989) *J Immunol Methods* 125:191-202; Mueller B M et al. (1990) *J Immunol* 144:1382-6. Chimeric mouse-human antibody, ch14.18, was found to have potent effector activities of antibody-dependent cellular cytotoxicity (ADCC) and complement-dependent cytotoxicity (CDC), as well as the ability to target GD2-positive melanoma cell xenografts in mice. Mueller et al. (supra).

An anti-GD2 antibody-IL2 fusion protein (immunocytokine) having IL2 fused to the light chain is genetically engineered. The immunocytokine contains the mouse 14.18 V regions, human immunoglobulin heavy and light chain constant (C) regions and a human IL2 sequence fused to the C-terminus of the light chain constant region. The human IL2 sequence is inserted in a vector containing the mouse 14.18 variable heavy ($V_H$) and variable light ($V_L$) coding sequences, as well as the constant heavy and light chain coding sequences. The IL2 coding sequence is fused in frame downstream and adjacent to the codon encoding the C-terminal amino acid of the light chain constant region. In some embodiments, the full length of the IL2 coding sequence is used. In some embodiments, a deletion, addition, or substitution of one or several N-terminal amino acids of IL2 is engineered and fused in-frame to the light chain C-terminal amino acid.

For example, the immunocytokine can be produced from a vector that encodes both heavy and light chains (e.g., light-chain fusions) on the same nucleic acid molecule. In some embodiments, splice sequences are included along with introns between the leader sequence used for each transcription unit (e.g., between V and C regions, and between the domains of the heavy chain constant regions. In some embodiments, one or more of the coding sequences are cDNA sequences (e.g., for IL2 or other cytokine). It should be appreciated that any suitable promoter may be used (e.g., CMV or other promoter).

Once all DNA sequences are assembled using the DNASTAR Lasergene 8 program, all coding sequences are checked to ensure there are no errors in coding the correct protein sequences during merging of input sequences. The final sequences are submitted to a contract supply organization with experience in gene synthesis and assembly (e.g., Blue Sky Biotech, Worcester, Mass.). After assembly, the sequence of the entire plasmid is verified and corrected, if necessary.

Multiple versions of the coding sequences with variations in the junction between to L chain C region, or other modification in the cytokine itself, may be tested for optimal expression and assembly into immunocytokines. Non-limiting examples include the following light-chain IL2 fusion proteins where sequence variations are underlined:

```
                                                    SEQ ID NO: 1
EIVMTQSPATLSVSPGERATLSCRSSQSLVHRNGNTYLHWYLQKPGQSPKLLIHK

VSNRFSGVPDRFSGSGSGTDFTLKISRVEAEDLGVYFCSQSTHVPPLTFGAGTKL

ELKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRGE

Captssstkktqlqlehllldlqmilnginnyknpkltrmltfkfympkkatelkhlqcl eeelkpleevlnlaqsknfhlrprdlisninvivlelkgsettfmceyadetativefln rwitfcqsiistlt
```

```
                                                    SEQ ID NO: 2
EIVMTQSPATLSVSPGERATLSCRSSQSLVHRNGNTYLHWYLQKPGQSPK

LLIHKVSNRFSGVPDRFSGSGSGTDFTLKISRVEAEDLGVYFCSQSTHVPPLTFGA

GTKLELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSF

NRGECaptssstkktqlqlehllldlqmilnginnyknpkltrmltfkfympkkatelkh lqcleeelkpleevlnlaqsknfhlrprdlisninvivlelkgsettfmceyadetativ eflnrwitfsqsiistlt
```

```
                                                    SEQ ID NO: 3
EIVMTQSPATLSVSPGERATLSCRSSQSLVHRNGNTYLHWYLQKPGQSPK

LLIHKVSNRFSGVPDRFSGSGSGTDFTLKISRVEAEDLGVYFCSQSTHVPPLTFGA

GTKLELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSF
```

-continued

```
NRGECQRVDaptssstkktqlqlehllldlqmilnginnyknpkltrmltfkfympkkat elkhlqcleeelkpleevlnlaqsknfhlrprdlisninvivlelkgsettfmceyadet ativeflnrwitfcqsiistlt
```

SEQ ID NO: 4

```
EIVMTQSPATLSVSPGERATLSCRSSQSLVHRNGNTYLHWYLQKPGQSPK

LLIHKVSNRFSGVPDRFSGSGSGTDFTLKISRVEAEDLGVYFCSQSTHVPPLTFGA

GTKLELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSF

NRGECQRVDaptssstkktqlqlehllldlqmilnginnyknpkltrmltfkfympkkat elkhlqcleeelkpleevlnlaqsknfhlrprdlisninvivlelkgsettfmceyadet ativeflnrwitfsqsiistlt
```

The resulting immunocytokines, a whole antibody HL chain dimer containing two molecules of IL2 per antibody, are produced in vitro from cells transfected with expression constructs encoding the immunocytokine heavy chain and light chain fusion protein.

Example 2

Production of Genetically Engineered Immunocytokines Having a Cytokine Fused to the C-Terminus of an Antibody Light Chain Expression vector DNA is used for transient expression of the protein in human 293F cells (InVitrogen) using standard protocols.

Before generating stable cell lines for long-term production of the anti-GD2 immunocytokine, the ability of the vector to express the desired protein is tested using transient expression and analysis of small amounts of the protein secreted from transfected cells. This is accomplished by producing milligram quantities of the plasmid DNA from the bacterial host and purifying the DNA using high resolution chromatography. Endotoxin-free DNA is used to transfect 293F cells in suspension culture and after several days of culture, the conditioned culture media is harvested. A small amount is incubated with protein A Sepharose beads by gentle mixing and then the captured protein is eluted in gel electrophoresis buffer. Half of the sample is treated further with reducing agent (β-mercaptoethanol) while the other half is not. Both samples are heated and analyzed by SDS polyacrylamide gel electrophoresis (SDS-PAGE) together with an immunoglobulin control protein. By using transient expression of non-Ig producing cells and eluting with gel buffer, it is possible to test the efficiency of the assembly process of the L-IL2 fusion protein. This is because 293 cells are capable of secreting both fully assembled molecules as well as H chain dimers that have not formed a disulfide bond with an L chain, but also bind to and elute from protein A. A correctly assembled IL2 based immunocytokine migrates as a single high molecular weight band on the gel (~200 Kd) when it is not reduced, but dissociates into two bands after chemical reduction. An H chain dimer migrated at approximately 100 kD.

Of the four sequences initially tested, two have no linker sequence between the C-terminal Cys of the L chain and the other two have a 4 amino acid spacer derived from the C terminus of dog C kappa. Unlike human C kappa, the dog light chain has these additional residues added after the Cys residue. Since it is known that these residues do not interfere with the assembly of H/L chains, it was thought according to aspects of the invention that they might promote the same process when included in an L chain fusion protein. Another initial consideration was the fact that native human IL2 has an unpaired Cys at position 125 and that this may interfere or compete for disulfide bound formation with the Cys located at the junction of the L chain and IL2. To test this, a construct of each linker type was constructed with either the native Cys or a Ser residue in position 125. This Cys to Ser mutation is well known in the art and is included in the commercially marketed IL2, Proleukin.

Following transient expression of 293F cells, and analysis of small samples by protein A capture and elution in SDS containing gel buffer, the most highly expressed and assembled constructs included those having sequences shown in SEQ ID NO: 1 and SEQ ID NO: 4. These represent a version with no linker and native Cys125 (SEQ ID NO: 1) and a version with the linker and modified Ser125 (SEQ ID NO: 4). For the other constructs, much lower amounts were made and a reduced proportion assembled into intact immunocytokines.

Transient cell cultures are scaled-up and moderate quantities of the immunocytokine are purified for further analyses. Multi-milligram quantities of the immunocytokine are purified from cell culture supernatants and captured using standard protein A Sepharose and ion exchange chromatography methods. This material is used to establish a reference standard for biochemical assays and for further characterization of biochemical and biophysical properties. Optimal proteins are intact, fully soluble at high concentration (e.g., greater that 1 mg/ml) and retain all biological activity after binding to protein A, elution at low pH, and subsequent neutralization with base. The material is used to establish enzyme-linked immunosorbent assay (ELISA) methods necessary for identity and potency assays, as well as for measurement of the immunocytokine in biological samples such as blood, plasma, or serum.

Based on the estimated amount of immunocytokine produced by transient expression in 293F cells, sufficient amounts of purified protein, needed for characterization and assay development, can be purified from between 100 ml and 1 L of culture using standard cell culture flasks or disposable wave bags. At least 1-2 mg of purified protein are prepared for further characterization and assay development.

The two constructs with the highest level of expression were scaled up to 100 ml cultures and the entire culture supernatants were captured on protein A and eluted using low pH. When these immunocytokines were characterized by SDS-PAGE under reducing and non-reducing conditions, only the construct containing SEQ ID NO: 1 broke down into the two chains representing the H and L-IL2 fusion chains, whereas the construct containing SEQ ID NO: 4 did not dissociate indicating that it had denatured during the low pH elution step from the protein A column.

In addition, stable cell line generation can be performed. Stable cell line generation in NS/0 mouse myeloma cells (or other suitable cell line, for example, CHO cells, etc.) is established using methotrexate as the selection marker. This is performed using linearized plasmid DNA restriction enzyme cut within the bacterial ampicillin resistance ($amp^R$) gene. DNA is introduced into the myeloma cells (or other suitable cells) using well established electroporation methods, and the cells are cultured in section medium containing 0.1 μM methotrexate. Drug-resistant myeloma clones are tested for secretion of immunocytokine using appropriate antisera. Expressing clones are tested for productivity, stability and growth rate. Subcloning is used to select for the optimal cell line properties.

The expressed protein, preferably secreted from cells growing in serum free media, is purified using established protocols for producing clinical grade protein. Great care is used to prevent endotoxin contamination. The steps may include a concentration step (e.g., tangential flow filtration), followed by binding to and elution from protein A Sepharose. After elution with acidic pH and neutralization, ion exchange chromatography can be used as a polishing step.

Purified protein is analyzed by SDS-PAGE and potential aggregation is examined by size-exclusion chromatography (SEC). Immunocytokine stability issues associated with aggregation are monitored closely. Current formulations, including lyophilization, that minimize stability issues are applied if necessary.

Conditioned media from the cultures (e.g., transient or stable expression cultures) can serve as a source of immunocytokine material for biochemical analyses to ensure that correctly sized proteins are secreted and that the H chain and L chain-IL2 fusion protein are assembled into a heterodimeric structure. The immunocytokine is captured on protein A Sepharose beads and subsequently analyzed by SDS-polyacrylamide gel electrophoresis. Media samples can be used to test for antigen binding activity as well as IL2 bioactivity, using a standard mouse cell line, CTLL-2, in a proliferation assay.

Pharmacokinetic properties can be determined in mice. Purified immunocytokine is used to measure concentration vs. time kinetics following intravenous dosing in mice. Blood samples are taken over a 24 hour period and the concentration of immunocytokine is measured by ELISA measuring both the antibody and enzyme-IL2 portion of the molecule. In some embodiments, the immunocytokine is captured using an anti-human IgG antisera, and the detection step uses a biotinylated anti-human IL2 antibody. This defines the amount of intact immunocytokine present in the samples.

Example 3

Figure 5:
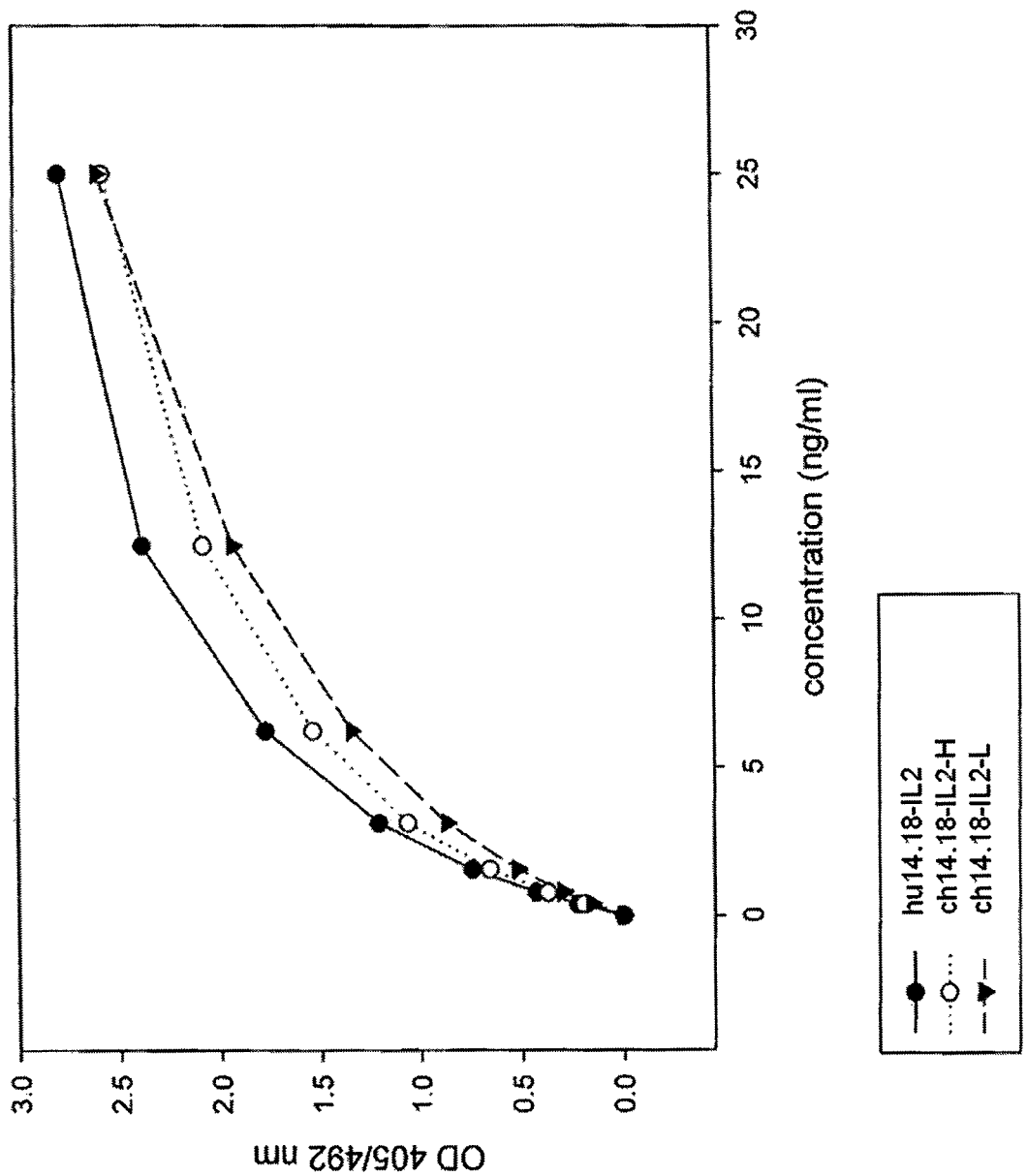
FIG. 5 shows binding of a light chain fusion construct to an anti-idiotype antibody and anti-IL2 antibodies in an ELISA.

Structure of an Immunocytokine Having a Cytokine Fused to the Light Chain Constant Region FIG. 5 shows that a fusion protein having a sequence shown in SEQ ID NO: 1 binds to both an anti-idiotype antibody (1A7) specific for the 14.18 antigen binding site and is detected in the bound state by an anti-IL2 antibody. This ELISA shows that IL2 is properly folded and exposed. The constructs tested are hu14.18-IL2 (humanized 14.18 with IL2 fused to the heavy chain); ch14.18-IL2-H (IL2 fused to the H chain but with a linker modification increasing half-life compared to hu14.18-IL2); and ch14.18-IL2-L containing the fusion protein of SEQ ID NO: 1 (IL2 fused to the light chain as described herein). The binding to the 1A7 antibody mimics binding to GD2 and is an easier assay to perform on a regular basis. It also indicated that the V regions are in their properly folded state for binding to GD2. Nonetheless, natural GD2 binding is also tested using tumor cells by flow cytometry and when testing effector functions (ADCC and CDC).

Antigen (e.g., GD2 or other antigen) binding can be used to evaluate the structure and function of the antigen-binding portion of the immunocytokine. In some embodiments, GD2 binding is performed using 96-well plates coated with GD2 (Calbiochem) and blocked with 5% bovine serum albumin (BSA) and 5% goat serum. Test antibody or antibody-containing culture supernatants are diluted in PBS containing 1% BSA and 1% goat serum and incubated in wells for 1 hour at room temperature. Unbound proteins are washed three times with dilution buffer and bound immunocytokine is detected with a horseradish peroxidase (HRP)-conjugated secondary antisera against the IgG and/or IL2 region of the protein. Bound HRP is quantitated by standard protocols.

An alternative method for testing GD2 binding is to incubate the test protein with a GD2-expressing cancer cell (e.g., melanoma) and to detect its binding using a secondary labeled antibody directed against the immunoglobulin or cytokine portion.

Similar assays may be used for evaluating the binding of other antigens.

Example 4

Figures 6A, 6B:
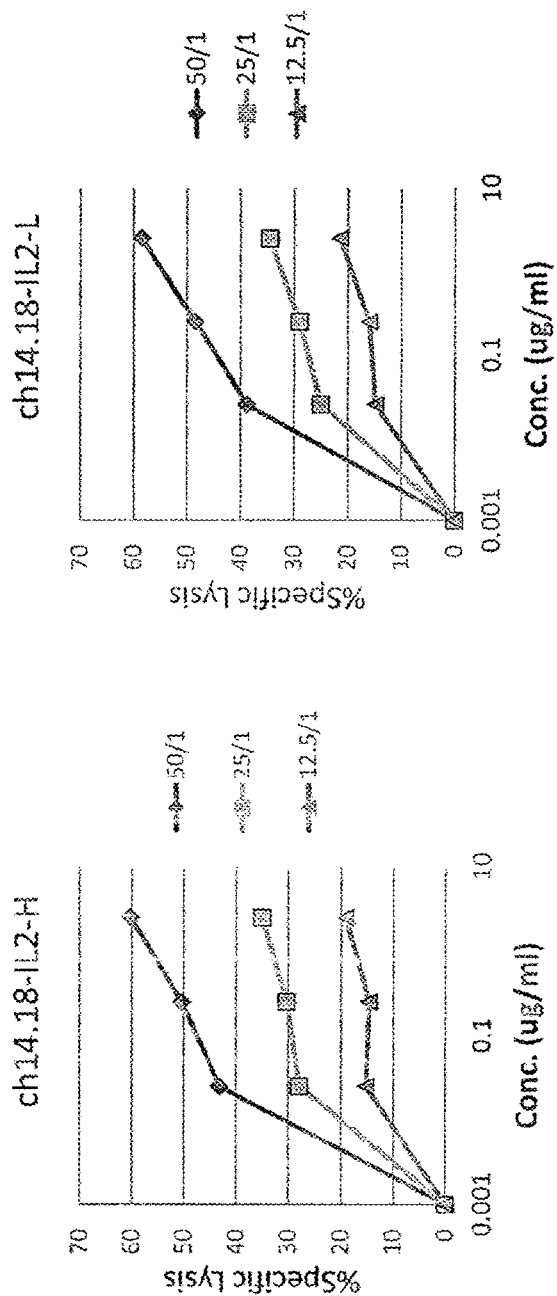
FIGS. 6A and 6B show the ADCC activity of a light chain fusion protein (FIG. 6B), and a heavy chain fusion protein (FIG. 6A)

ADCC Activity of an Immunocytokine Having a Cytokine Fused to the Light Chain Constant Region FIG. 6 shows that the ADCC activity of a light chain fusion protein is the same as that of a heavy chain fusion protein. The constructs tested are an H-fusion with a chimeric 14.18-IL2 (ch14.18-IL2-H) and a L-fusion with chimeric 14.18-IL2 (ch14.18-IL2-L). The test system is M21 human melanoma target cells expressing GD2 and labeled with $^{51}Cr$ and human PBMC as effectors. Such cell preparations contain roughly 5-10% NK cells, the primary mediators of ADCC activity in vitro.

The ability of the immunocytokine to mediate the effector function of ADCC (antibody-dependent cellular cytotoxicity) was tested using peripheral blood mononuclear cells at different effector to target ratios and a human GD2 expressing melanoma cell line. Target cells were incubated with $^{51}Cr$ and then washed to remove free isotope. Isolated peripheral blood lymphocytes from a healthy human volunteer were incubated with labeled target cells for 4 hours in the absence or presence of increasing amounts of the immunocytokine and the amount of release chromium was taken as a measure of specific lysis.

Example 5

Figure 7:
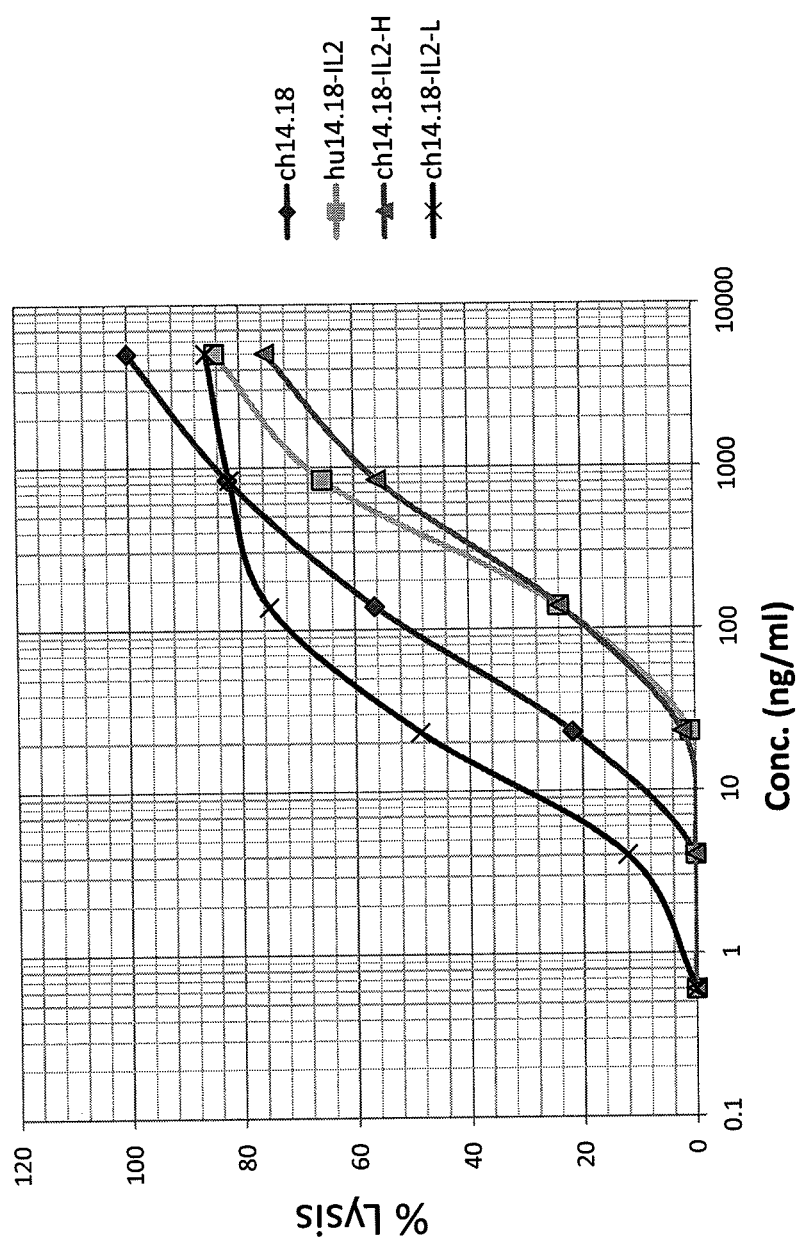
FIG. 7 shows the relative CDC activities of a light chain fusion protein (L-fusion), the native antibody (without a cytokine fusion), and corresponding heavy chain fusion proteins (H-fusion)

CDC Activity of an Immunocytokine Having a Cytokine Fused to the Light Chain Constant Region FIG. 7 shows that the CDC activity of a light chain fusion protein is much higher than that of the native antibody (without a cytokine fusion) and the immunocytokines in which IL2 is fused to the H chains (H-fusion with a humanized 14.18, and H-fusion with a chimeric 14.18). This dramatic difference between H and L chain fusion constructs is highly significant because of the overall limitation of dose levels of IL2 immunocytokines (due to IL2 toxicity), such that levels sufficient to engage this effector mechanism in vivo may be quite limited or require doses associated with unwanted side effects.

Example 6

Cytokine Activity of an Immunocytokine Having a Cytokine Fused to the Light Chain Constant Region The following molecules were tested for their IL2 activity: recombinant IL2, originally from Chiron (now marketed by Prometheus Therapeutics and Diagnostics), recombinant IL2 from Hoffman-La Roche, ch14.18-IL2-H heavy chain fusion (H-fusion with a chimeric 14.18), and ch14.18-IL2-L light chain fusion (L-fusion) containing SEQ ID NO: 1.

IL2 bioactivity is performed in 96 well plates containing CTLL-2 mouse T cells that have been deprived of IL2 for 48 hour prior to the assay. These cells respond to IL2 through binding to the high affinity IL2 receptor. Dilutions of purified proteins and culture media containing immunocytokines are plated and then mixed with CTLL-2 cells in culture medium and incubated for two days at 37° C. Additional medium containing $^3$H-thymidine is added and incubation continued for an additional 16 hours. Incorporation of $^3$H is measured using standard protocols. The extent to which the fused IL2 induces proliferation via the mouse IL2 receptor is evaluated based on the amount of $^3$H incorporation.

Figure 8:
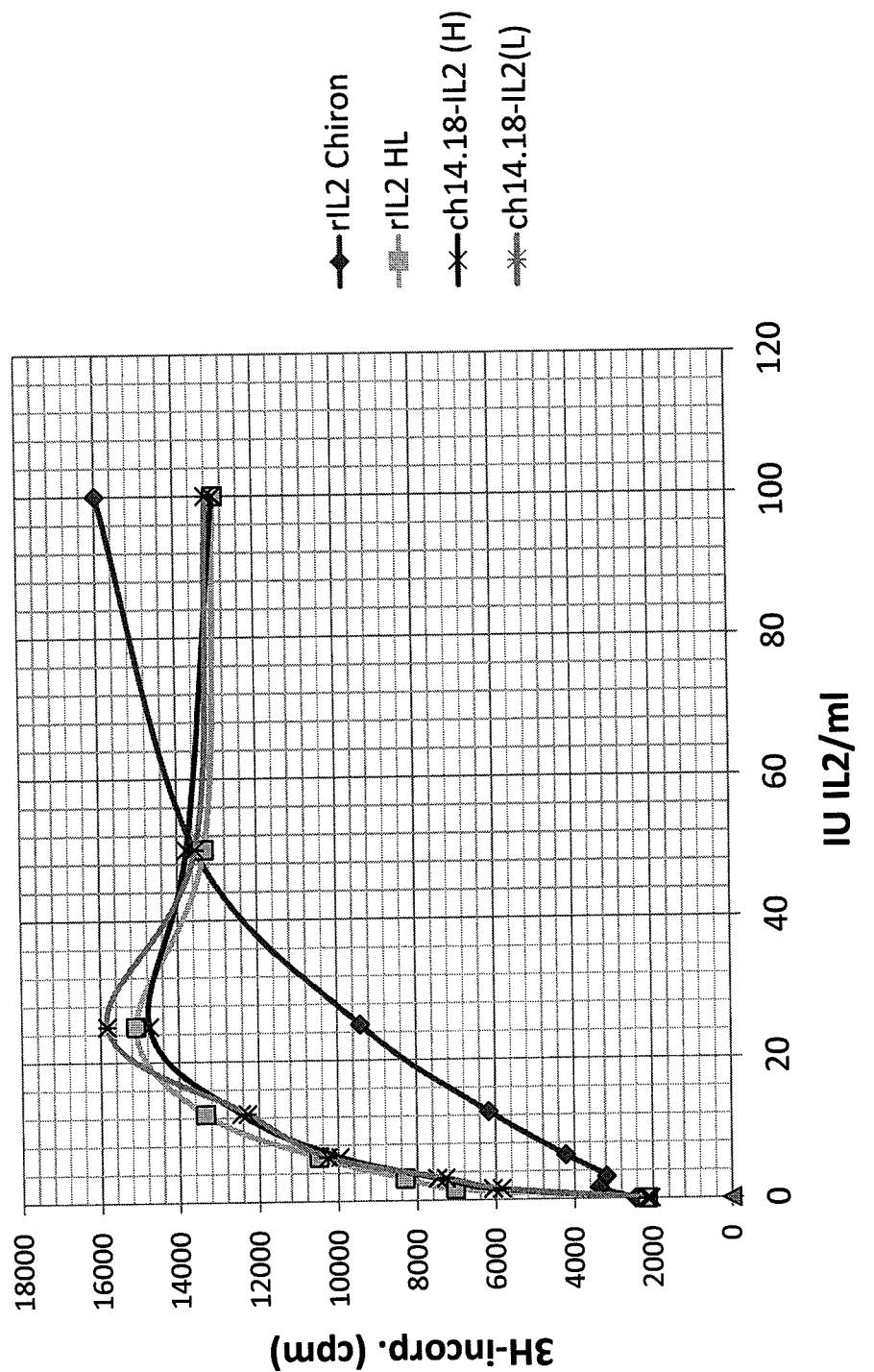
FIG. 8 shows the relative IL2 bioactivity of IL2 fused to the C-terminus of a light chain constant region, and recombinant IL2 (not fused to a cytokine)

The results are shown in FIG. 8. IL2 fused to the C-terminus of the light chain constant region is at least as active as recombinant IL2 (not fused to a cytokine) and the IL2 fused to the heavy chain in ch14.18-IL2-H in the IL2 bioactivity assay. This shows that the fusion to the C-terminus of the light chain constant region does not have any significant effect on the function of IL2 and its interaction with the high affinity IL2 receptor. Similar results are expected with other cytokines, including for example, similar cytokines that have approximately the same distance between the junction with the C terminus of the light chain and the first critical receptor contact point.

It should be appreciated that mutant cytokines also can be developed with enhanced, reduced or receptor-specific activity and evaluated using methods known in the art and described herein.

The functional properties of cytokines can be evaluated using any appropriate assay. For example a T cell proliferation assay may be used. Peripheral blood mononuclear cells (PBMC) are isolated from approximately 100 mL of normal human blood (Irwin Memorial Blood Bank, San Francisco, Calif.) diluted 1:2 in cold Dulbecco's phosphate buffered saline ($Ca^{2+}$ and $Mg^{2+}$ free; DPBS). Ficoll-Paque (Pharmacia) is underlayed and the sample is centrifuged to isolate the PBMC, followed by extensive washes in cold DPBS. PHA blasts (activated T cells) are generated by resuspending cells in RPMI 1640 containing 10% fetal bovine serum (Hyclone), to which 1% (w/v) of each of the following is added: L-glutamine; non-essential amino acids; sodium pyruvate; and antibiotic-antimycotic (RPMI media) at a density of $10^6$ cells/ml. Phytohemmaglutanin (PHA-P; Sigma) is added at a final concentration of 10 µg/mL, and cells are incubated at 37 C., 5% $CO^2$ for 3 days. Cells are harvested and washed two times in DPBS, resuspended in RPMI media and plated into 96-well flat bottom plates at a density of $10^5$ cells/well in 200 µl with varying concentrations of IL2 or variant immunocytokine in RPMI media. Plates are incubated for 48 hours at 37 C., pulsed with 1 µCi $^3$H-thymidine (DuPont NEN®, Boston, Mass.)/well for 6 hours, harvested, and radioactivity was measured after harvesting cells onto glass fiber filters.

In some embodiments, an NK cell proliferation assay may be used. Peripheral blood mononuclear cells (PBMC) are isolated from approximately 100 mL of normal human blood (Irwin Memorial Blood Bank, San Francisco, Calif.) diluted 1:2 in cold Dulbecco's phosphate buffered saline ($Ca^{2+}$ and $Mg^{2+}$ free; DPBS). Ficoll-Paque (Pharmacia) is underlayed and the sample is centrifuged to isolate the PBMC, followed by extensive washes in cold DPBS. NK cells are separated from other cells. The Miltenyi Biotec's NK cell isolation kit (Bergisch Gladbach, Germany; Cat#465-01) can be used for this purpose. The kit consists of two reagents, separation columns and a very powerful magnetic column support. The first reagent is a cocktail of hapten conjugated monoclonal CD3, CD4, CD19, CD33 antibodies of mouse IgG1 isotype. This is to deplete the PMBC of T cells, B cells and myeloid cells. It is envisioned that any suitable set of antibodies recognizing these cell types can be used. The second reagent consists of colloidal super-paramagnetic MACs microbeads conjugated to an anti-hapten antibody. Cells are resuspended in PBS with 0.5% bovine serum albumin and 2 mM EDTA (PBS/EDTA). The volume of the suspension is dependent on the number of cells used and is provided in a chart by Miltenyi Biotec. Typically, with a cell number of 2 to 5 $10^8$ PBMC, the cells are resuspended in 800 µL of the buffer and then 200 µL of each reagent is used. After incubation with the reagents, the cells are added to the column (resuspended in 2 mls of buffer). The non-NK cells adhere to the magnet (depleted) and the NK cells are isolated and collected in the flow through. Cells are washed, resuspended in RPMI media (contains: RPMI 1640, to which 1% of each of the following is added: L-glutamine; non-essential amino acids, sodium pyruvate; antibiotic-antimycotic (all from Gibco/BRL, Gaithersburg, Md.); 10% fetal bovine serum (Hyclone)), and plated into 96-well flat bottom plates at a density of $10^5$ cells/well in 200 µl. Cells are harvested and washed two times in DPBS, resuspended in RPMI media and plated into 96-well flat bottom plates at a density of $10^5$ cells/well in 200 µl with varying concentrations of IL2 or immunocytokine variant in RPMI media Plates were incubated for 48 hours at 37 C., pulsed with 1 µCi $^3$H-thymidine (DuPont NEN®, Boston, Mass.)/well for 6 hours, harvested, and radioactivity is measured after harvesting cells onto glass fiber filters.

Example 7

Figure 9:
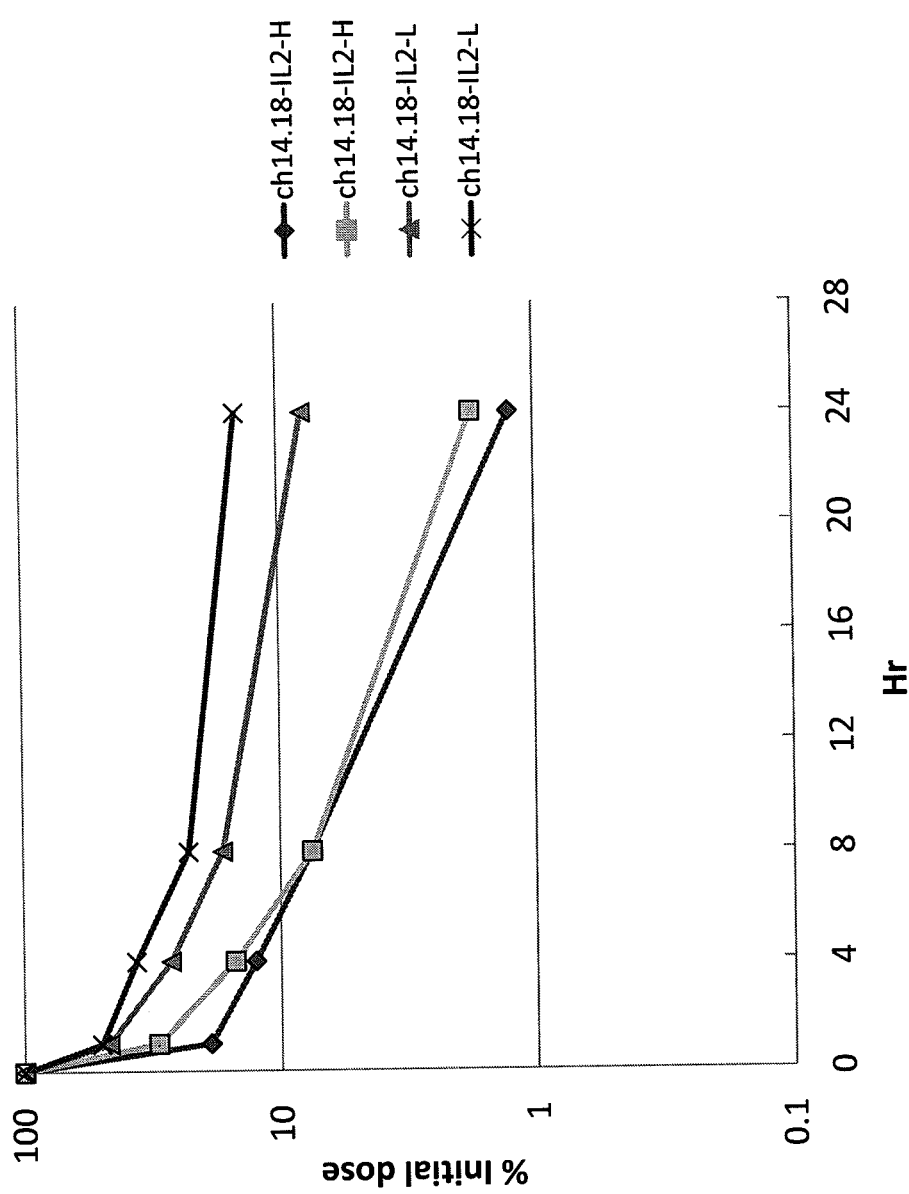
FIG. 9 shows the relative pharmacokinetic profile of an L-fusion protein, and a H-fusion protein.

PK of an Immunocytokine Having a Cytokine Fused to the Light Chain Constant Region FIG. 9 shows that an IL2 L-fusion with a chimeric 14.18 has a more favorable pharmacokinetic profile than an optimized IL2 H-fusion with a chimeric 14.18. This version has a linker modification that increases the half-life of immunocytokines in which IL2 is fused to the H chain.

In some embodiments, the pharmacokinetics of IL2 fusion proteins may be assayed in mice as follows. For example, three 6 to 8 week old mice are used. 25 µg of the fusion proteins, diluted to 125 µg/ml in PBS, are injected in the tail vein of mice, and 50 µl blood samples are obtained by retro-orbital bleeding immediately after injection (0 hours) and at 0.5, 1, 2, 4, 8, and 24 hours post injection. Blood samples are collected in heparin-coated tubes to prevent blood clotting, and immunocytokine levels in the post-cellular plasma supernatant are measured in an ELISA assay. The procedure of the ELISA assay used for pharmacokinetic studies has been previously described (WO01/58957). Capture of an immunocytokine from plasma can be carried out on antigen-coated (e.g., GD2 or EpCAM-coated plates) and the detection can be performed with an HRP-conjugated antibody directed against IL2. In other embodiments, the capture reagent is a polyclonal goat anti-human IgG antisera and the detection is a biotinylated mouse anti-human IL2 conjugate that is subsequently quantitated using a streptavidin-HRP conjugate.

In some embodiments, the pharmacokinetics of IL2 fusion proteins may be assayed in mice as follows. Mice are injected in the tail vein with approximately 10 µg of a 14.18-IL2 immunocytokine molecule and sampled immediately thereafter by retro-orbital bleeding to establish the $t_0$ point. Additional samples are taken at 15, 30, 60 min, 2, 4, 8, 24 and 48 hour. Serum is prepared from blood samples by standard protocols and stored cold until assayed. A specific ELISA for measuring intact immunocytokine is modified from an existing protocol (Gan J, et al., Specific enzyme-linked immunosorbent assays for quantitation of antibody-cytokine fusion proteins. Clin Diagn Lab Immunol. 6(2): 23642, 1999) and is based on capture in a 96-well plate coated with an anti-idiotype antibody (1A7) specific for the 14.18 antibody, followed by detection of any captured protein with an anti-IL2 specific antisera.

Example 8

Figure 10:
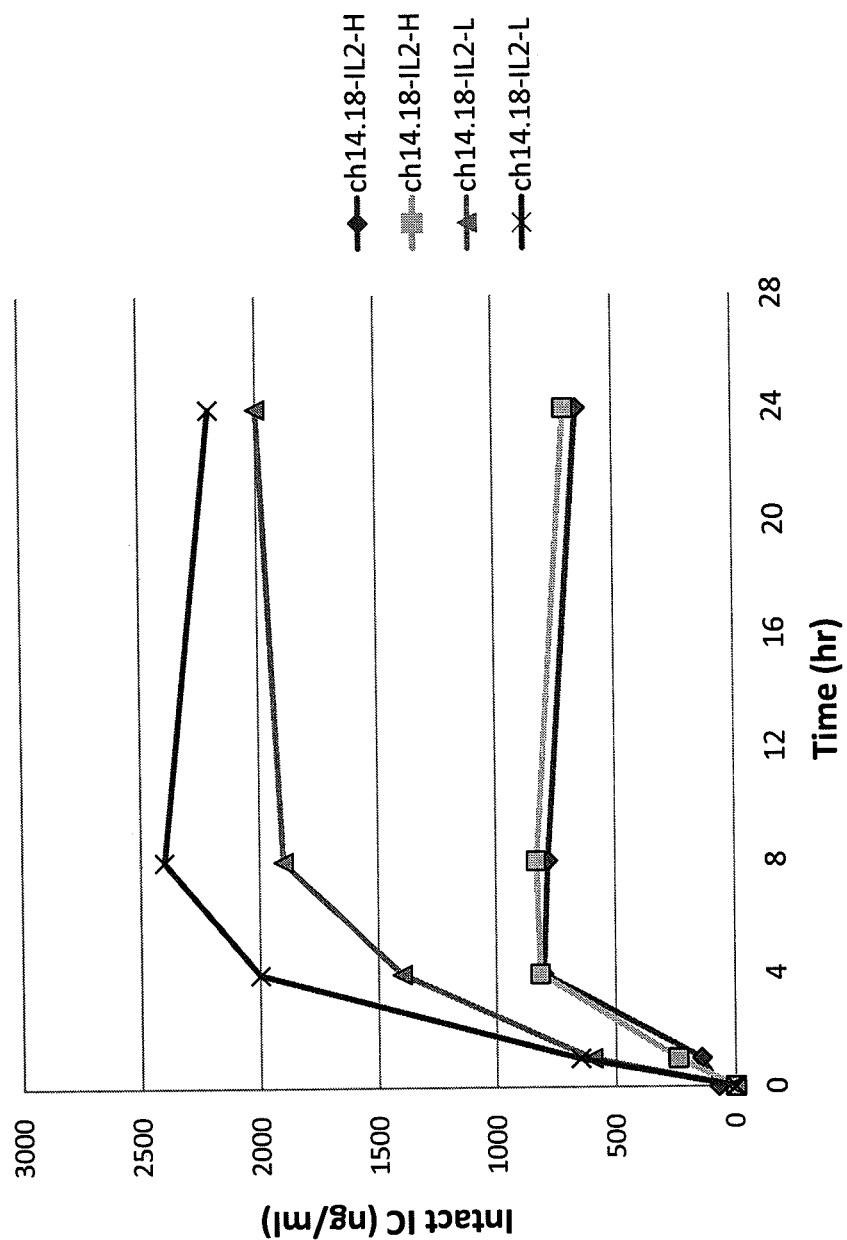
FIG. 10 shows the subcutaneous bioavailability of an L-fusion protein, and a H-fusion protein.

Subcutaneous Bioavailability of an Immunocytokine Having a Cytokine Fused to the Light Chain Constant Region FIG. 10 shows that ch14.18-IL2 light chain fusion (L) has a higher subcutaneous bioavailability than ch14.18-IL2 heavy chain fusion (H). This may be due to reduced uptake and intracellular degradation by FcR-bearing cells in the lymphatic compartment. It is known that proteins injected subcutaneously are taken up by the lymphatic system and then emerge slowly into the bloodstream as a function of whether or not they are taken up by cells in that compartment. Reduced degradation by FcR-bearing cells in the lymphatic compartment and therefore increased and/or extended release into the bloodstream.

Example 9

Immunocytokines Containing Other Cytokines Having Similar Structures

Immunocytokines containing other cytokines fused to the light chain C-termini can be generated. For example, IL-7, IL-15, IL-15-IL15Rα fusion protein, IL-21, IFNα, GM-CSF and other cytokines may be used.

These immunocytokines may be generated and evaluated using methods described herein. For example, their structural and functional properties may be evaluated using assays and controls described herein. In addition, assays for evaluating the activity of other cytokines are known to one of skill in the art and may be used to evaluate the cytokine activity in an immunocytokine having the cytokine fused to the C-terminus of the light chain constant region. In some cases, depending on the particular cytokine, it may be necessary to add a linker peptide or shorten the junction length for optimal immunocytokine assembly and cytokine bioactivity and to test variants of such linkers using the methods described herein.

Example 10

Target Specific Immunocytokines Containing Shielded Cytokines that are Unmasked and Exposed and Activated Upon Target Antigen Binding FIG. 3 illustrates how a cytokine (or active residues within a cytokine) can be shielded or masked by the conformation of an immunocytokine in the absence of binding to an antigen-expressing target cell as described in more detail herein.

In some embodiments, light chain immunocytokine fusions can be designed to mask or shield (at least partially) the cytokine, thereby reducing its activity, in the absence of binding to a cell that expresses a target antigen. Unlike the C-terminus of the IgG H chain, the C-terminus of the L chain is constrained by the disulfide bond formed between the terminal Cys residue and the Cys in the H chain (e.g., in IgG1 and IgG3 based light chain immunocytokine fusion proteins). Accordingly, when a polypeptide such as a cytokine is fused to this C-terminus and assembled into an intact immunocytokine, the N-terminal portion of the cytokine is expected to be constrained too. This property can be used to reduce the biological activity of the polypeptide (e.g., cytokine) in the unbound configuration of the antibody fusion protein or to confer receptor specificity.

In some embodiments, an immunocytokine is designed to reduce the length and/or flexibility of the junction of the C-terminus of the light chain and the N-terminus of the cytokine. For example, one or more N-terminal amino acids of the cytokine may be removed.

It should be appreciated that in some embodiments deletions are made in a flexible N-terminal region, or portion thereof, that is not required for function of the cytokine. For example, an IL2 or other cytokine may have 1-10, 1-5, 4, 3, or 2, N-terminal amino acids deleted. In some embodiments, upon binding to a target cell expressing an antigen of interest, the conformational change of the antibody exposes a contact residue, e.g., the Asp20 of IL2, and thereby activates the cytokine (e.g., IL2) portion of the immunocytokine.

Two non-limiting examples of fusion proteins that were designed to demonstrate this effect have the following amino acid sequences:

SEQ ID NO: 5
EIVMTQSPATLSVSPGERATLSCRSSQSLVHRNGNTYLHWYLQKPGQSPK

LLIHKVSNRFSGVPDRFSGSGSGTDFTLKISRVEAEDLGVYFCSQSTHVPPLTFGA

GTKLELKRTVAAPSVFIFPPSDEQLKSGTASVVCLLNNFYPREAKVQWKVDNAL

```
QSGNSQESVTEQDSKDSTYSLSSTLTLSKADYEKHKVYACEVTHQGLSSPVTKSF

NRGECaptstqlqlehllldlqmilnginnyknpkltrmltfkfympkkatelkhlqcle eelkpleevlnlaqsknfhlrprdlisninvivlelkgsettfmceyadetativeflnr witfcqsiistlt
```

SEQ ID NO: 6
```
EIVMTQSPATLSVSPGERATLSCRSSQSLVHRNGNTYLHWYLQKPGQSPK

LLIHKVSNRFSGVPDRFSGSGSGTDFTLKISRVEAEDLGVYFCSQSTHVPPLTFGA

GTKLELKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSF

NRGECtqlqlehllldlqmilnginnyknpkltrmltfkfympkkatelkhlqcleeelk pleevlnlaqsknfhlrprdlisninvivlelkgsettfmceyadetativeflnrwitf cqsiistlt
```

SEQ ID NO: 5 has IL2 residues 5-9 deleted (but retains the highly conserved N-terminal APTS sequence preserved), whereas SEQ ID NO: 6 has IL2 residues 1-9 deleted, and therefore brings the first alpha helix closer to the disulfide bond between the H and L chains involving the C-terminal Cys of the L chain.

Similar design considerations may be used for other cytokines, for example, cytokines having an important Asp residue or other important amino acid within the N-terminal approximately 20-30 amino acids (e.g., IL-7, IL-15, IL-21, IFNα).

It should be appreciated that similar design considerations may be used for other antibody fusion proteins where a protein other than a cytokine is fused to the C-terminus of the light chain. In some embodiments, proteins having an important active residue at or near the N-Terminus may have their activity shielded by fusion to the C-Terminus of the light chain. However, it should be appreciated that depending on the relative distance between the active residue and the fusion junction, the length of the protein may need to be adjusted (e.g., by deletion of one or several non-essential N-Terminal amino acids or by addition of one or several linker amino acids, in order to obtain a desired ratio of activity between the unbound and target-cell-bound antibody fusion.

Examples of activity ratios between unbound and target-cell-bound antibody fusion include 1:2; 1:5; 1:10; 1:50; 1:100; 1:1,000; and lower, higher, or intermediate ratios.

In vitro and/or cellular binding assays may be used to evaluate the extent to which target antigen binding (e.g., to antigens on a target cell) activates a cytokine fused to the light chain of an immunocytokine.

In some embodiments, an anti-idiotype antibody may be used in solution to expose and/or activate a masked fusion peptide (e.g., a cytokine). For example, an immunocytokine may be mixed in solution with an anti-idiotype antibody and added at different dilutions to a preparation of responder cells to determine the activity profile of the immunocytokine.

In some embodiments, an anti-idiotype antibody may be attached to a solid support such as a bead or a plate, blocked and contacted with different amounts of immunocytokine and exposed to a fixed number of responder cells. Alternatively, the immunocytokine can be bound to antigen-expressing tumor cells that are subsequently irradiated (to prevent proliferation) and exposed to responder cells. See, for example, Hank et al., Clin. Cancer Res., 1996, vol. 2, pp. 1951-1959, the disclosure of which is incorporated herein by reference. It should be appreciated that the activity of bound relative to unbound (e.g., based on a standard unbound assay) can be calculated to determine whether binding increases the activity of the fused cytokine.

Example 11

Assays for Identifying Immunocytokines Having Altered Cytokine Specificity

In some embodiments, immunocytokines described herein may have altered specificity (e.g., different relative effects on the production and/or activation of natural killer cells and/or the production and/or activation of cytotoxic T-cells) relative to non-fused cytokines. Assays for evaluating cytokine specificities are known in the art. A useful cell line expressing the intermediate, but not the high affinity IL2 receptor, is called TF-1β and is dependent on IL2 or other exogenous cytokines for growth and survival. Proliferation of this cell line can also be measured using convenient non-radioactive dyes such as Alamar Blue and Presto Blue, and others. TF-1β cells were maintained in RPMI medium containing 10% fetal calf serum, and rIL2 (50 IU/ml). On the day of the assay, cells were collected by centrifugation and re-suspended in RPMI without IL2. Test proteins were diluted in RPMI without IL2 and placed in serial wells of a 96-well plate in duplicate. TF-1β cell suspension (100 ul at $10^5$ cells/ml) was added to all wells and the plate was incubated at 37° C. for 48 hour, after which Presto Blue (20 ul/well—InVitrogen) was added to all wells. After al hour incubation at 37° C., the fluorescence generated by mitochondrial reduction was measured using a Tecan GENios Pro fluorescent plate reader (535 nm excitation and 590 nm emission). The same exact assay is performed using the mouse CTLL-2 cell line to determine activity mediated through the high affinity IL2 receptor and a comparison of results defines the degree of receptor selectivity. This approach was used to test the potential receptor selectivity of ch14.18-L-IL2 immunocytokines with several variant sequences and compared to the H-chain fusion protein (ch14.18-H-IL2). The latter molecule is known to have no receptor selectivity when compared to free rIL2.

Figure 11:
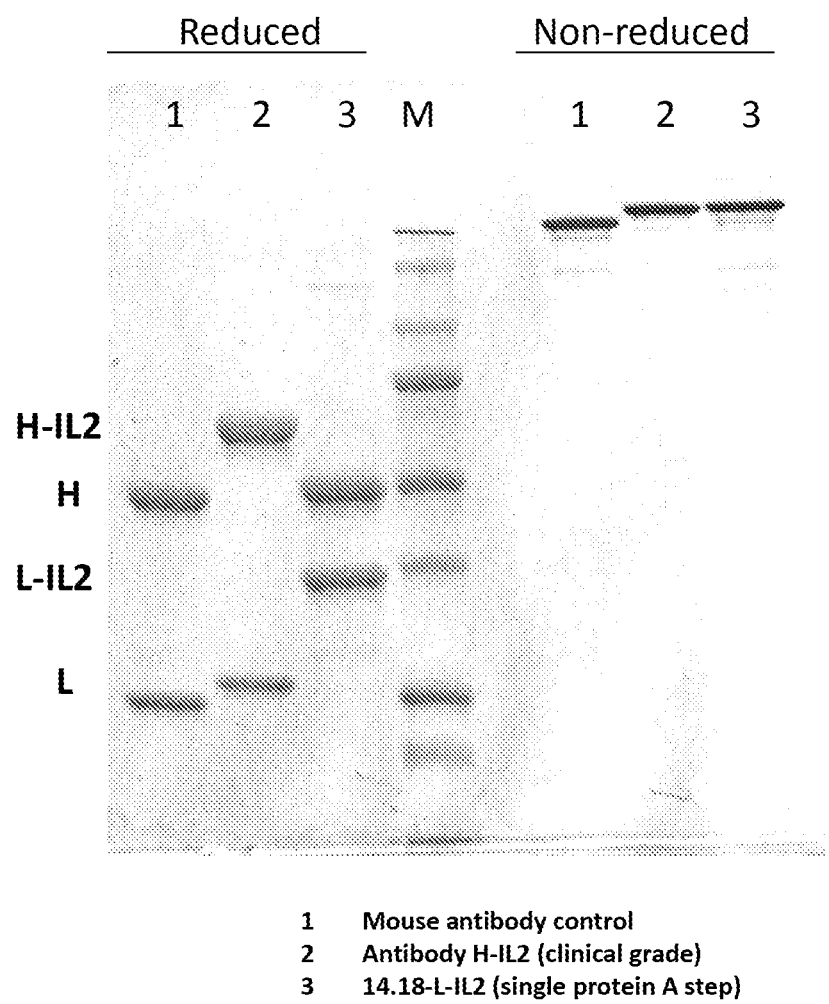
FIG. 11 shows a gel of reduced and non-reduced fusion constructs demonstrating that the light chain fusion construct forms complete heterodimers stabilized by disulfide bonds between the L and H chain and between H chains.

Using these two cell lines as indicators for receptor specificity, a number of constructs were tested for bioactivity in the non-radioactive bioassay and the concentrations needed to induce half maximal proliferation was used to determine the ED50. These molecules were produced by the transient transfection of HEK 293 cells either in suspension, or in tissue culture plates, and all were purified by binding to and elution from protein A Sepharose. Some of these molecules also were produced and purified from stably transfected NS/0 myeloma cells. After a one-step purification from cell culture medium the molecules were analyzed by SDS-PAGE and found to be fully assembled and to be stabilized with the proper disulfide bonds (FIG. 11). Individual proteins showed identical bioactivity whether they were produced in mouse NS/0 or human HEK293 cells. Due to the variability of these cell based assays, they were repeated multiple times.

| Immunocytokine | CTLL-2 (high aff) ED$_{50}$ (ng/ml) | TF-1β (Int aff) ED$_{50}$ (ng/ml) | Relative Activity High aff/ Inter Aff | Selectivity for High Affinity Receptor |
| --- | --- | --- | --- | --- |
| H-IL2 | 0.9-2.0 | 7.0-9.0 | 1.0/1.0 | 1 |
| L-IL2 SEQ ID NO: 1 | 1.0-2.0 | 65-66 | 1.0/0.12 | 8.3 |
| L-IL2 SEQ ID NO: 3 | 1.5 | 10 | 1.0/0.8 | 1.25 |
| L-IL2 SEQ ID NO: 5 | 0.8-2.0 | >500 | 1.0/0.01 | >100 |
| L-IL2 SEQ ID NO: 6 | 0.7-2.0 | >500 | 1.0/0.01 | >100 |
| L-IL2 SEQ ID NO: 10 | 1.0-2.0 | >500 | 1.0/0.01 | >100 |

Table 1 shows the potency of each construct for each cell line, and the relative potency based on the receptor type is shown.

```
                                                        SEQ ID NO: 1
------------Cys-X19-D20---------------------Q126-----
                                                        SEQ ID NO: 3
------------Cys-QRVD-X19-D20----------------Q126-----
                                                        SEQ ID NO: 10
------------Cys-X19-D20---------------------W126-----
                                                        SEQ ID NO: 5
------------Cys-X14-D20---------------------Q126-----
                                                        SEQ ID NO: 6
------------Cys-X10-D20---------------------Q126-----
```

Table 2 illustrates the sequences of the constructs that were used.

Surprisingly, the construct containing SEQ ID NO: 1 was shown to have significantly reduced activity using the TF-1β cell line (intermediated receptor), while maintaining normal activity on the CTLL-2 line (as demonstrate in the radioactive thymidine uptake assay). This approximate 8-fold specificity was highly reproducible in several individual assays and suggests that this molecule could have significantly reduced side effects compared to a similar molecule with full activity against the intermediate receptor. In contrast, a construct containing SEQ ID NO: 3 (with a 4 residue spacer between the C terminal Cys and the first residue of IL2) had full activity against the intermediate receptor. This strongly suggests that the distance between the Cys residue junction and the beta chain contact residue, D20, determines the activity against the intermediate receptor as a function of its accessibility to the IL2 receptor. It should be appreciated that other spacer sequences may be used. This distance dependence is demonstrated further using constructs with shorter distances between the C terminal Cys and D20. Constructs containing SEQ ID NO: 5 and SEQ ID NO: 6 (with 5 and 9 residue deletions, respectively, and originally designed to be inactive prior to antigen binding), showed no detectable activity using the TF-1β cell line up to the highest concentrations tested. Still another approach was tested with respect to gaining increased specificity for the high versus the intermediate affinity IL2 receptor. In this case, a mutation in a residue known to contact the IL2 receptor gamma chain (Q126W), was combined with the construct containing SEQ ID NO: 1 to create SEQ ID NO: 10. This combines two relatively modest reductions in intermediate receptor binding to the two chains of this complex (beta and gamma) but the consequence was a dramatic reduction in activity. Despite this dramatic effect of the intermediate receptor, there was no reduction at all in the activity against the high affinity receptor with this construct or any of the other constructs listed in Table 1.

Example 12

Assays for Identifying Immunocytokines Having Intermediate Levels of Cytokine Activity Immunocytokine variants may be constructed by fusing an antibody light chain to cytokine variants having different lengths of N-terminal deletions, as described above. Variants that are identified as having intermediate levels of cytokine activity (e.g., between full activity and no activity) may have masked activity due to the conformation of the immunocytokine. In some embodiments, cytokine activity may increase upon antigen binding as illustrated in FIG. 3. Accordingly, immunocytokine variants having intermediate levels of activity (e.g., between 1% and 99%, between 10% and 90%, between 20% and 80%, between 30% and 70%, around 50%, of full activity, or other level of reduced activity) may be candidates for testing in assays described above to determine whether cytokine the activity is increased upon antigen binding (e.g., upon binding to a target cell expressing the target antigen).

In some embodiments, fusion variants with intermediate levels of cytokine activity may be identified using one or more cell based assays.

For example, N-terminal deletion variants of IL2 fused to the light chain of an antibody and having mutations in key contact residues with the high affinity receptor (e.g., R38 and F42 may be evaluated in IL2 bioactivity assays. The degree of overall cytokine bioactivity or specific receptor activity can be modified by the combinatorial effect of these individual receptor interactions—one based on the distance between the light chain C terminal Cys residue and the D20 contact point and the second based on the other contact residue. In most cases, amino acid substitutions with only modest effect on their own could be sufficient to have potent effects in combination.

Example 13

Analysis of IL2 Activity and Receptor Specificity of Immunocytokines with the Cytokine Fused to the C Terminus of Light Chain after Binding to Antigen-Coated Beads In order to simulate the target cell microenvironment in which an immunocytokine is bound to a cell surface, magnetic beads were coupled with an anti-idiotype antibody, 1A7, that recognizes the idiotype of the 14.18 anti-GD2 antibody, and in this way mimics the GD2 antigen. A Dynabead Antibody Coupling Kit (Invitrogen Dynal AS, Oslo, Norway) was used to couple 100 ug of 1A7 antibody to approximately 10 mg of dry beads according to the manufacturer's instructions. The final preparation contained 1 mg of coupled beads per ml of suspension with the expected amount of 50 ng of antibody per microliter of bead suspension. Immunocytokine mixtures contained 200 ng of each protein, 8 microliters of beads (400 ng of anti-idiotype antibody in a final volume of 200 microliters containing RPMI medium with 10% fetal bovine serum but no IL2 (growth medium). The mixtures were incubated under different conditions but all gave similar results. These include room temperature for 2 hours in sterile Eppendorf tubes on a rotating wheel; 1 hur at 37° C. in wells of a 96 well plate; and 1 hour at 37 degrees in a bound bottom plastic cryovial, with occasional mixing. After incubation the beads were recovered with a magnet and washed in 0.5 ml growth medium and re-suspended in the same. A control immunocytokine with full IL2 activity against both receptor types, but no ability to bind the 1A7 anti-idiotype antibody, was used to demonstrate that bioactivity is dependent on antigen binding. Bead-immunocytokine complexes were gently mixed and each added to duplicate wells of a 96-well plate, after which two-fold dilutions were made by transferring 100 microliter volumes down a series of wells containing 100 microliters of growth medium. A suspension of responder cells containing $10^5$ cells/ml was added to all wells (100 microliters/well) and the plates were incubated for 2-3 days at 37° C. Cell growth was measured by using Presto Blue Cell Viability Reagent (Invitrogen) as described above. This method was used to compare the activity of bound immunocytokines constructed either as a heavy chain fusion (14.18-IL2-H) or a light chain fusion (14.18-IL2-L). The latter molecule contained SEQ ID NO: 1, which showed a selectivity of binding to the high affinity receptor of about 8-fold (due to loss of activity against the intermediate form) when tested as a soluble protein. In the bound form, there was only a slight loss of activity using TF-1β cells where it differed from the 14.18-IL2-H molecule by less than two fold in multiple experiments.

Figure 12:
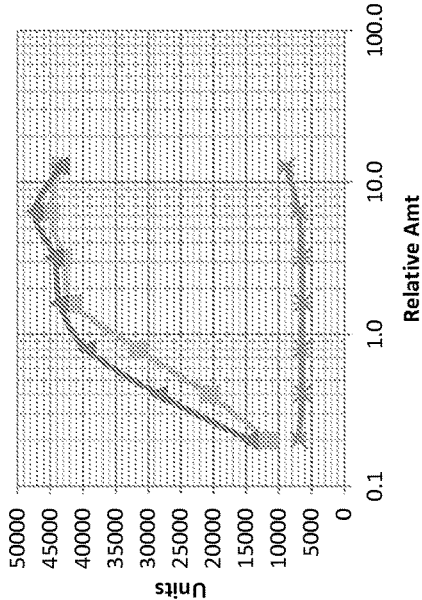
FIG. 12 shows relative activation of intermediate and high affinity receptors with different fusion constructs bound to antigen coated beads.
Figure 12:
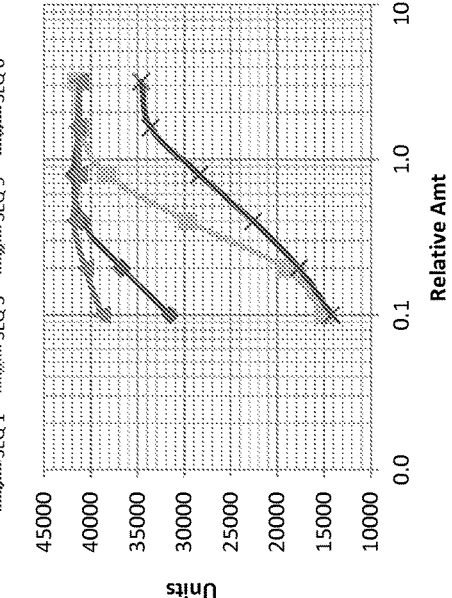
Figure 12:
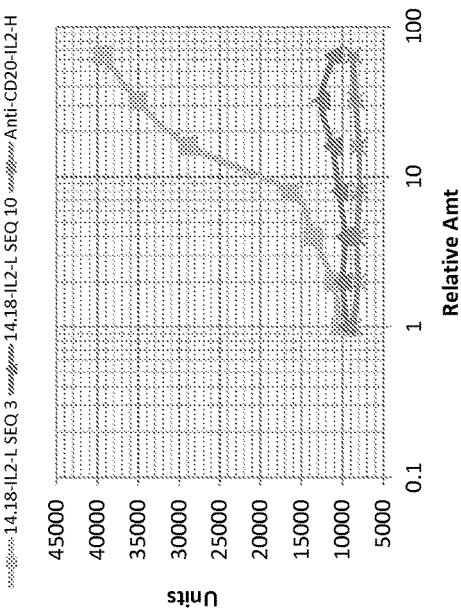
Figure 12:
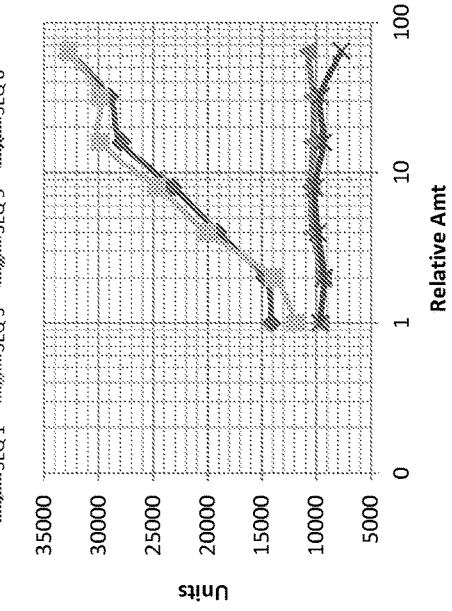

Additional assays were performed in the same manner using the various immunocytokines. In two such experiments the suspensions of beads bound to immunocytokines (0.5 ml) were added to plates with TF-1β cells (0.2 ml×2) and the remaining 0.1 ml suspensions were diluted 5-fold and added to a second 96-well plate to which CTLL-2 cells were added. The first experiment compared 14.18-IL2-L molecules containing either SEQ ID NO: 3 (fully active for both receptors in solution) or SEQ ID NO: 10 (fully active for the high affinity receptor and inactive for the intermediate receptor). A fully active immunocytokine that does not bind the 1A7 anti-idiotype antibody on the beads was included to test whether unbound immunocytokines were responsible for the resulting proliferation activity. As shown in FIG. 12A, the non-binding immunocytokine had no activity in either the TF-1β or CTLL-2 assay, demonstrating that only bound immunocytokines are providing the proliferative signals. When the two 14.18-IL2-L immunocytokines were bound to beads the one with SEQ ID NO: 3 was very active with both cells lines while the one with SEQ ID NO: 10 was only active in inducing CTLL-2 proliferation, closely reflecting what was seen in their soluble forms. A second experiment (FIG. 12B) compared the activities of the 14.18-IL2-L molecules that differed by the distances between their fusion junction (the C terminal Cys of the L chain) and the D20 residue of IL2. The molecule with the longest distance (SEQ ID NO: 3) had the highest activity against the intermediate receptor (TF-1β cells) in solution (8-fold higher than the one with SEQ ID NO: 1) but was only slightly higher when bound to beads. This is similar to what was seen with the 14.18-IL2-H molecule discussed above. The molecules with deletions of 5 or 9 residues in the N terminus of IL2 (SEQ ID NO: 5 and SEQ ID NO: 6) had little or no activity in either the soluble or bound forms suggesting that this distance is too short to allow access of the receptor to the D20 contact point even when bound to antigen. When the same bead mixtures were tested with CTLL-2 cells, all of them showed activity that was close to or far more potent to the molecule with normal activity and specificity in solution (SEQ ID NO: 3). The molecule with the shortest distance (SEQ ID NO: 6) had the lowest, but still significant activity, while the molecules that were shorter by 4 (SEQ ID NO: 1) or 9 (SEQ ID NO: 5) residues were significantly more active against the high affinity IL2 receptor when presented in the bound form.

These results demonstrate that this fusion approach allows for a unique way to modulate bioactivity in a way that does not require protein mutations or can be combined with mutagenesis to create additional molecules with unique properties. While only the molecule with SEQ ID NO: 3 showed a difference in bioactivity against the intermediate IL2 receptor as a consequence antigen binding, additional molecules with slightly shorter distances between the fusion junction and D20 could show more dramatic differences than seen with this molecule. Alternatively, molecules with a slightly longer distance (e.g., plus one or two or more residues) and a point mutation in a receptor contact residue such as Q126, N88, R38 or F42 may show activity differences between soluble and bound forms thereby identifying candidate fusions having increased activity upon antigen binding (e.g., cell-surface antigen binding).

Example 14

Construction of a Bi-Specific Antibody in which a scFv Recognizing a Cell Surface Antigen is Fused to the C Terminus of the Light Chain Anti-CD3 antibodies are capable of triggering human T cell proliferation, especially in combination with a second signal such as anti-CD28 binding or exogenous IL2. They are also capable of triggering target cell lysis when used as part of a bi-specific antibody, together with an antibody recognizing a molecule on the target cell surface. Most bi-specific antibodies are mono-specific and are composed of antibody fragments resulting in short circulating half-lives. This is to avoid cross-linking of T cells in the circulation with a bi-valent molecule, before the molecule binds to the cell surface. Due to the possible steric hindrance afforded by the fusion to the light chain, and the possible release of this block upon cell surface binding, an attempt was made to make bivalent, whole antibody fusion protein.

Such a molecule could have a long circulating half-life and potentially not present itself to T-cells until it has bound to the target cell surface. A fusion sequence encoding the variable regions of the anti-CD3 antibody, OKT3, was synthesized so that it would encode an in-frame fusion protein with the human C kappa (SEQ ID NO: 11). The DNA encoding this protein was inserted into a vector also encoding the 14.18 H chain and the plasmid was use to transiently transfect HEK 293 cells with lipofectamine. After 72 hour of incubation, the fusion protein in the culture supernatant was purified by binding to and elution from protein A Sepharose beads and analyzed by denaturing SDS-PAGE with and without the addition of reducing agent. Unlike the IL2 fusions to the light chain, this construct did not form a complete molecule that was stabilized by disulfide bonds between the two H chains, although its binding to protein A suggests that it formed a non-covalent heterodimer. In order to improve this and other similar constructs, additional fusion can be made using the first several amino acid residues of IL2 as a linker sequence, since the constructs containing this sequence all formed complete heterodimer molecules stabilized with disulfide bonds. A non-limiting example is provided as SEQ ID NO: 12 which contains the first seven amino acid residues of IL2 between the C terminal Cys of the L chain and the first residue of the scFv. The number of these residues necessary to form a stable structure can easily be tested by someone skilled in the art. Once a sequence is identified that allows for such stable constructs, the resulting bi-specific molecules can be tested for binding to T cells expressing CD3 and triggering a biological response. The ability to trigger a response can be compared using molecules in solution to ones that have been immobilized to beads coated with antigen (or a surrogate anti-idiotype antibody). If it becomes necessary to shorten the junction between the C terminal Cys residue of the L chain and the antibody binding regions in order to mask activity, this can be accomplished by systematically removing residues of the V region framework while leaving the optimized IL2 linker intact. Resulting molecules are compared in their soluble and immobilized forms to identify one that is inactive in solution but active once bound to antigen. For example, freshly isolated human PBMC are cultured with dilutions of the soluble or bead bound bi-specific molecules, together with a known synergistic concentration anti-CD28 antibody in solution. After 48 hour the incorporation of 3H-thymidine is used to measure T cell proliferation, similar to what was described in example 6. When a suitable molecule is identified, it can be tested for its ability to induce the lysis of an antigen expressing target cell using resting human T cells (freshly prepared PBMC are one source) as effector cells. Lysis can be assessed by chromium release as described above for ADCC assays, or by using non-radioactive dyes (e.g., Total Cytotoxicity Test, Immunochemistry Technologies, Bloomington, Minn.), or release of LDH (CytoTox96, Promega).

Non-Limiting Nucleotide and Amino Acid Sequences

In some embodiments, a light chain fusion protein has an amino acid sequence shown in one the following non-limiting sequences. Light chain sequences are shown in upper case letters (with the variable region italicized) and the fusion peptide is shown in lower case letters. In non-limiting embodiments, the light chain sequence contains a 14.18 mouse variable region, and a human light chain constant region. In some non-limiting embodiments, a light chain is fused to a human IL2 sequence. Non-limiting amino acid sequence variants of the IL2 sequence are underlined in lower case letters. A non-limiting 4 amino acid spacer is underlined in upper case letters for SEQ ID NOs: 3 and 4. A non-limiting 7 amino acid peptide corresponding to the N-terminus of IL2 is underlined in lower case italic letters in SEQ ID NO: 12.

SEQ ID NO: 1
*EIVMTQSPATLSVSPGERATLSCRSSQSLVHRNGNTYLHWYLQKPGQSPKLLIHKVSNR*

*FSGVPDRFSGSGSGTDFTLKISRVEAEDLGVYFCSQSTHVPPLTFGAGTKLELKRTVA*

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECaptssstkk tqlqlehllldlqmilnginnyknpkltrmltfkfympkkatelkhlqcleeelkpleev lnlaqsknfhlrprdlisninvivlelkgsettfmceyadetativeflnrwitf<u>c</u>qsii stlt

SEQ ID NO: 2
*EIVMTQSPATLSVSPGERATLSCRSSQSLVHRNGNTYLHWYLQKPGQSPKLLIHKVSNR*

*FSGVPDRFSGSGSGTDFTLKISRVEAEDLGVYFCSQSTHVPPLTFGAGTKLELKRTVA*

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECaptssstkk tqlqlehllldlqmilnginnyknpkltrmltfkfympkkatelkhlqcleeelkpleev lnlaqsknfhlrprdlisninvivlelkgsettfmceyadetativeflnrwitf<u>s</u>qsii stlt

SEQ ID NO: 3
*EIVMTQSPATLSVSPGERATLSCRSSQSLVHRNGNTYLHWYLQKPGQSPKLLIHKVSNR*

*FSGVPDRFSGSGSGTDFTLKISRVEAEDLGVYFCSQSTHVPPLTFGAGTKLELKRTVA*

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECQRVDa ptssstkktqlqlehllldlqmilnginnyknpkltrmltfkfympkkatelkhlqclee elkpleevlnlaqsknfhlrprdlisninvivlelkgsettfmceyadetativeflnrw itfcqsiistlt

SEQ ID NO: 4
EIVMTQSPATLSVSPGERATLSCRSSQSLVHRNGNTYLHWYLQKPGQSPKLLIHKVSNR

FSGVPDRFSGSGSGTDFTLKISRVEAEDLGVYFCSQSTHVPPLTFGAGTKLELKRTVA

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECQRVDa ptssstkktqlqlehllldlqmilnginnyknpkltrmltfkfympkkatelkhlqclee elkpleevlnlaqsknfhlrprdlisninvivlelkgsettfmceyadetativeflnrw itfsqsiistlt

SEQ ID NO: 5
EIVMTQSPATLSVSPGERATLSCRSSQSLVHRNGNTYLHWYLQKPGQSPKLLIHKVSNR

FSGVPDRFSGSGSGTDFTLKISRVEAEDLGVYFCSQSTHVPPLTFGAGTKLELKRTVA

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECaptstqlql ehllldlqmilnginnyknpkltrmltfkfympkkatelkhlqcleeelkpleevlnlaq sknfhlrprdlisninvivlelkgsettfmceyadetativeflnrwitfcqsiistlt

SEQ ID NO: 6
EIVMTQSPATLSVSPGERATLSCRSSQSLVHRNGNTYLHWYLQKPGQSPKLLIHKVSNR

FSGVPDRFSGSGSGTDFTLKISRVEAEDLGVYFCSQSTHVPPLTFGAGTKLELKRTVA

APSVFIFPPSDEQLKSGTASVVCLLNNFYPREAKVQWKVDNALQSGNSQESVTE

QDSKDSTYSLSSTLTLSKADYEKHKVYACEVTHQGLSSPVTKSFNRGECtqlqlehlll dlqmilnginnyknpkltrmltfkfympkkatelkhlqcleeelkpleevlnlaqsknfh lrprdlisninvivlelkgsettfmceyadetativeflnrwitfcqsiistlt SEQ ID NO: 7
Mouse 14.18 H chain variable region:
EVQLLQSGPELEKPGASVMISCKASGSSFTGYNMNWVRQNIGKSLEWIGAIDPY

YGGTSYNQKFKGRATLTVDKSSSTAYMHLKSLTSEDSAVYYCVSGMEYWGQG

TSVTVSS

SEQ ID NO: 8
Variable region of the mouse 14.18 L chain (this sequence
represent a hybrid V region containing an original 14.18
hybridoma sequence having the first framework region
switched with that of another V region to obtain good
expression - see Gillies et al., J Immunol Methods, 125:
191-202, 1989 - this non-limiting sequence was used for the
constructs exemplified herein):
EIVMTQSPATLSVSPGERATLSCRSSQSLVHRNGNTYLHWYLQKPGQSPKLLIHK

VSNRFSGVPDRFSGSGSGTDFTLKISRVEAEDLGVYFCSQSTHVPPLTFGAGTKL

ELK

SEQ ID NO: 9
gb|AAC82527.1| immunoglobulin gamma-1 heavy chain constant
region [Homo sapiens]
STKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPP

CPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLS

PGK

SEQ ID NO: 10
EIVMTQSPATLSVSPGERATLSCRSSQSLVHRNGNTYLHWYLQKPGQSPKLLIHKVSNR
FSGVPDRFSGSGSGTDFTLKISRVEAEDLGVYFCSQSTHVPPLTFGAGTKLELKRTVA
APSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGECaptssstkk
tqlqlehllldlqmilnginnyknpkltrmltfkfympkkatelkhlqcleeelkpleev
lnlaqsknfhlrprdlisninvivlelkgsettfmceyadetativeflnrwitfcwsii
stlt SEQ ID NO: 11
EIVMTQSPATLSVSPGERATLSCRSSQSLVHRNGNTYLHWYLQKPGQSPKLLIHKVSNR
FSGVPDRFSGSGSGTDFTLKISRVEAEDLGVYFCSQSTHVPPLTFGAGTKLELKRTVA
APSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGECqvqlqqsg
aelarpgasvkmsckasgytftrytmhwvkqrpgqglewigyinpsrgytnynqkfkdka
tlttdksstaymqlssltsedsavyycaryyddhycldywgqgttltvssggggsgggg
sggggsdiqivltqspaimsaspgekvtmtcsasssysymnwyqqksgtspkrwiydtsk
lasgvpahfrgsgsgtsysltisgmeaedaatyycqqwssnpftfgsgtklein SEQ ID NO: 12
EIVMTQSPATLSVSPGERATLSCRSSQSLVHRNGNTYLHWYLQKPGQSPKLLIHKVSNR
FSGVPDRFSGSGSGTDFTLKISRVEAEDLGVYFCSQSTHVPPLTFGAGTKLELKRTVA
APSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGECaptssstqv
qlqqsgaelarpgasvkmsckasgytftrytmhwvkqrpgqglewigyinpsrgytnynq
kfkdkatlttdksstaymqlssltsedsavyycaryyddhycldywgqgttltvssggg
gsggggsggggsdiqivltqspaimsaspgekvtmtcsasssysymnwyqqksgtspkrw
iydtsklasgvpahfrgsgsgtsysltisgmeaedaatyycqqwssnpftfgsgtklein

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A fusion protein comprising a cytokine which is:
   (i) IL2,
   (ii) human IL2,
   (iii) human IL2, wherein the length of the N-terminal region of the cytokine fusion is shortened by 1 to 10 amino acids of the N-terminal region of SEQ ID NO: 13, or
   (iv) IL2 having a mutation at one or more positions corresponding in human IL2 of SEQ ID NO: 13 to D20, F42, R38, N88, or Q126;
   wherein the fusion protein retains cytokine activity, and wherein the fusion protein comprises one antibody comprising two heterodimers, each heterodimer comprising
   a) a full-length antibody heavy chain, and
   b) a full-length antibody light chain fused at its C-terminus, without a linker peptide, to the cytokine,
   wherein each heterodimer comprises only a single cytokine, and
   wherein the antibody specifically binds to an antigen expressed on the extracellular surface of a tumor cell.

2. The fusion protein of claim 1, wherein the full-length antibody heavy chain is an IgG heavy chain.

3. The fusion protein of claim 2, wherein the IgG heavy chain is an IgG$_1$ heavy chain.

4. The fusion protein of claim 2, wherein the IgG heavy chain is an IgG$_2$ or IgG$_3$ or IgG$_4$ heavy chain.

5. The fusion protein of claim 1, wherein the light chain constant region is a Cκ constant region.

6. The fusion protein of claim 1, wherein the light chain constant region is a Cλ constant region.

7. A composition comprising the fusion protein of claim 1.

8. A pharmaceutical composition comprising (i) a therapeutically effective amount of the fusion protein of claim 1, and (ii) a pharmaceutically acceptable carrier.

* * * * *

SEQUENCE LISTING

```
<160> NUMBER OF SEQ ID NOS: 13

<210> SEQ ID NO 1
<211> LENGTH: 353
<212> TYPE: PRT
<213> ORGANISM: Artificial Sequence
<220> FEATURE:
<223> OTHER INFORMATION: Synthetic Polypeptide
```

<400> SEQUENCE: 1

```
Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Ala Pro Thr Ser
    210                 215                 220

Ser Ser Thr Lys Lys Thr Gln Leu Gln Leu Glu His Leu Leu Leu Asp
225                 230                 235                 240

Leu Gln Met Ile Leu Asn Gly Ile Asn Asn Tyr Lys Asn Pro Lys Leu
                245                 250                 255

Thr Arg Met Leu Thr Phe Lys Phe Tyr Met Pro Lys Lys Ala Thr Glu
            260                 265                 270

Leu Lys His Leu Gln Cys Leu Glu Glu Glu Leu Lys Pro Leu Glu Glu
        275                 280                 285

Val Leu Asn Leu Ala Gln Ser Lys Asn Phe His Leu Arg Pro Arg Asp
    290                 295                 300

Leu Ile Ser Asn Ile Asn Val Ile Val Leu Glu Leu Lys Gly Ser Glu
305                 310                 315                 320

Thr Thr Phe Met Cys Glu Tyr Ala Asp Glu Thr Ala Thr Ile Val Glu
                325                 330                 335

Phe Leu Asn Arg Trp Ile Thr Phe Cys Gln Ser Ile Ile Ser Thr Leu
            340                 345                 350

Thr
```

<210> SEQ ID NO 2
<211> LENGTH: 353
<212> TYPE: PRT
<213> ORGANISM: Artificial Sequence
<220> FEATURE:
<223> OTHER INFORMATION: Synthetic Polypeptide

<400> SEQUENCE: 2

Glu Ile Val Met Thr Gln Ser Pro Ala Thr Leu Ser Val Ser Pro Gly
1               5                   10                  15

Glu Arg Ala Thr Leu Ser Cys Arg Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Ala Pro Thr Ser
210                 215                 220

Ser Ser Thr Lys Lys Thr Gln Leu Gln Leu Glu His Leu Leu Leu Asp
225                 230                 235                 240

Leu Gln Met Ile Leu Asn Gly Ile Asn Asn Tyr Lys Asn Pro Lys Leu
                245                 250                 255

Thr Arg Met Leu Thr Phe Lys Phe Tyr Met Pro Lys Lys Ala Thr Glu
            260                 265                 270

Leu Lys His Leu Gln Cys Leu Glu Glu Glu Leu Lys Pro Leu Glu Glu
        275                 280                 285

Val Leu Asn Leu Ala Gln Ser Lys Asn Phe His Leu Arg Pro Arg Asp
290                 295                 300

Leu Ile Ser Asn Ile Asn Val Ile Val Leu Glu Leu Lys Gly Ser Glu
305                 310                 315                 320

Thr Thr Phe Met Cys Glu Tyr Ala Asp Glu Thr Ala Thr Ile Val Glu
                325                 330                 335

Phe Leu Asn Arg Trp Ile Thr Phe Ser Gln Ser Ile Ile Ser Thr Leu
            340                 345                 350

Thr

<210> SEQ ID NO 3
<211> LENGTH: 357
<212> TYPE: PRT
<213> ORGANISM: Artificial Sequence
<220> FEATURE:
<223> OTHER INFORMATION: Synthetic Polypeptide

<400> SEQUENCE: 3

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gln Arg Val Asp
210                 215                 220

Ala Pro Thr Ser Ser Thr Lys Lys Thr Gln Leu Gln Leu Glu His
225                 230                 235                 240

Leu Leu Leu Asp Leu Gln Met Ile Leu Asn Gly Ile Asn Asn Tyr Lys
                245                 250                 255

Asn Pro Lys Leu Thr Arg Met Leu Thr Phe Lys Phe Tyr Met Pro Lys
            260                 265                 270

Lys Ala Thr Glu Leu Lys His Leu Gln Cys Leu Glu Glu Glu Leu Lys
        275                 280                 285

Pro Leu Glu Glu Val Leu Asn Leu Ala Gln Ser Lys Asn Phe His Leu
290                 295                 300

Arg Pro Arg Asp Leu Ile Ser Asn Ile Asn Val Ile Val Leu Glu Leu
305                 310                 315                 320

Lys Gly Ser Glu Thr Thr Phe Met Cys Glu Tyr Ala Asp Glu Thr Ala
                325                 330                 335

Thr Ile Val Glu Phe Leu Asn Arg Trp Ile Thr Phe Cys Gln Ser Ile
            340                 345                 350

Ile Ser Thr Leu Thr
        355

<210> SEQ ID NO 4
<211> LENGTH: 357
<212> TYPE: PRT
<213> ORGANISM: Artificial Sequence
<220> FEATURE:
<223> OTHER INFORMATION: Synthetic Polypeptide

<400> SEQUENCE: 4

```
Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gln Arg Val Asp
    210                 215                 220

Ala Pro Thr Ser Ser Ser Thr Lys Lys Thr Gln Leu Gln Leu Glu His
225                 230                 235                 240

Leu Leu Leu Asp Leu Gln Met Ile Leu Asn Gly Ile Asn Asn Tyr Lys
                245                 250                 255

Asn Pro Lys Leu Thr Arg Met Leu Thr Phe Lys Phe Tyr Met Pro Lys
            260                 265                 270

Lys Ala Thr Glu Leu Lys His Leu Gln Cys Leu Glu Glu Glu Leu Lys
        275                 280                 285

Pro Leu Glu Glu Val Leu Asn Leu Ala Gln Ser Lys Asn Phe His Leu
    290                 295                 300

Arg Pro Arg Asp Leu Ile Ser Asn Ile Asn Val Ile Val Leu Glu Leu
305                 310                 315                 320

Lys Gly Ser Glu Thr Thr Phe Met Cys Glu Tyr Ala Asp Glu Thr Ala
                325                 330                 335

Thr Ile Val Glu Phe Leu Asn Arg Trp Ile Thr Phe Ser Gln Ser Ile
            340                 345                 350

Ile Ser Thr Leu Thr
            355

<210> SEQ ID NO 5
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 5
```

```
Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Ala Pro Thr Ser
210                 215                 220

Thr Gln Leu Gln Leu Glu His Leu Leu Leu Asp Leu Gln Met Ile Leu
225                 230                 235                 240

Asn Gly Ile Asn Asn Tyr Lys Asn Pro Lys Leu Thr Arg Met Leu Thr
                245                 250                 255

Phe Lys Phe Tyr Met Pro Lys Lys Ala Thr Glu Leu Lys His Leu Gln
            260                 265                 270

Cys Leu Glu Glu Glu Leu Lys Pro Leu Glu Glu Val Leu Asn Leu Ala
        275                 280                 285

Gln Ser Lys Asn Phe His Leu Arg Pro Arg Asp Leu Ile Ser Asn Ile
        290                 295                 300

Asn Val Ile Val Leu Glu Leu Lys Gly Ser Glu Thr Thr Phe Met Cys
305                 310                 315                 320

Glu Tyr Ala Asp Glu Thr Ala Thr Ile Val Glu Phe Leu Asn Arg Trp
                325                 330                 335

Ile Thr Phe Cys Gln Ser Ile Ile Ser Thr Leu Thr
            340                 345

<210> SEQ ID NO 6
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 6

Ile Val Met Thr Gln Ser Pro Ala Thr Leu Ser Val Ser Pro Gly Glu
1               5                   10                  15
```

```
Arg Ala Thr Leu Ser Cys Arg Ser Ser Gln Ser Leu Val His Arg Asn
            20                  25                  30

Gly Asn Thr Tyr Leu His Trp Tyr Leu Gln Lys Pro Gly Gln Ser Pro
        35                  40                  45

Lys Leu Leu Ile His Lys Val Ser Asn Arg Phe Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Leu Gly Val Tyr Phe Cys Ser Gln Ser Thr
                85                  90                  95

His Val Pro Pro Leu Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Thr Gln Leu Gln Leu
    210                 215                 220

Glu His Leu Leu Leu Asp Leu Gln Met Ile Leu Asn Gly Ile Asn Asn
225                 230                 235                 240

Tyr Lys Asn Pro Lys Leu Thr Arg Met Leu Thr Phe Lys Phe Tyr Met
                245                 250                 255

Pro Lys Lys Ala Thr Glu Leu Lys His Leu Gln Cys Leu Glu Glu Glu
            260                 265                 270

Leu Lys Pro Leu Glu Glu Val Leu Asn Leu Ala Gln Ser Lys Asn Phe
        275                 280                 285

His Leu Arg Pro Arg Asp Leu Ile Ser Asn Ile Asn Val Ile Val Leu
    290                 295                 300

Glu Leu Lys Gly Ser Glu Thr Thr Phe Met Cys Glu Tyr Ala Asp Glu
305                 310                 315                 320

Thr Ala Thr Ile Val Glu Phe Leu Asn Arg Trp Ile Thr Phe Cys Gln
                325                 330                 335

Ser Ile Ile Ser Thr Leu Thr
            340

<210> SEQ ID NO 7
<211> LENGTH: 113
<212> TYPE: PRT
<213> ORGANISM: Mus musculus

<400> SEQUENCE: 7

Glu Val Gln Leu Leu Gln Ser Gly Pro Glu Leu Glu Lys Pro Gly Ala
1               5                   10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45
```

Gly Ala Ile Asp Pro Tyr Tyr Gly Gly Thr Ser Tyr Asn Gln Lys Phe
            50                  55                  60

Lys Gly Arg Ala Thr Leu Thr Val Asp Lys Ser Ser Ser Thr Ala Tyr
 65                  70                  75                  80

Met His Leu Lys Ser Leu Thr Ser Glu Asp Ser Ala Val Tyr Tyr Cys
                 85                  90                  95

Val Ser Gly Met Glu Tyr Trp Gly Gln Gly Thr Ser Val Thr Val Ser
                100                 105                 110

Ser

<210> SEQ ID NO 8
<211> LENGTH: 113
<212> TYPE: PRT
<213> ORGANISM: Mus musculus

<400> SEQUENCE: 8

Glu Ile Val Met Thr Gln Ser Pro Ala Thr Leu Ser Val Ser Pro Gly
 1               5                  10                  15

Glu Arg Ala Thr Leu Ser Cys Arg Ser Ser Gln Ser Leu Val His Arg
                20                  25                  30

Asn Gly Asn Thr Tyr Leu His Trp Tyr Leu Gln Lys Pro Gly Gln Ser
            35                  40                  45

Pro Lys Leu Leu Ile His Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
                100                 105                 110

Lys

<210> SEQ ID NO 9
<211> LENGTH: 329
<212> TYPE: PRT
<213> ORGANISM: Homo sapiens

<400> SEQUENCE: 9

Ser Thr Lys Gly Pro Ser Val Phe Pro Leu Ala Pro Ser Ser Lys Ser
 1               5                  10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
 50                  55                  60

Ser Ser Val Val Thr Val Pro Ser Ser Ser Leu Gly Thr Gln Thr Tyr
 65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val

```
                130                 135                 140
Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
                290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 10
<211> LENGTH: 353
<212> TYPE: PRT
<213> ORGANISM: Artificial Sequence
<220> FEATURE:
<223> OTHER INFORMATION: Synthetic Polypeptide

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
                20                  25                  30

Asn Gly Asn Thr Tyr Leu His Trp Tyr Leu Gln Lys Pro Gly Gln Ser
            35                  40                  45

Pro Lys Leu Leu Ile His Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
              165                 170                 175
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Ala Pro Thr Ser
        210                 215                 220

Ser Ser Thr Lys Lys Thr Gln Leu Gln Leu Glu His Leu Leu Leu Asp
225                 230                 235                 240

Leu Gln Met Ile Leu Asn Gly Ile Asn Asn Tyr Lys Asn Pro Lys Leu
                245                 250                 255

Thr Arg Met Leu Thr Phe Lys Phe Tyr Met Pro Lys Lys Ala Thr Glu
            260                 265                 270

Leu Lys His Leu Gln Cys Leu Glu Glu Glu Leu Lys Pro Leu Glu Glu
        275                 280                 285

Val Leu Asn Leu Ala Gln Ser Lys Asn Phe His Leu Arg Pro Arg Asp
    290                 295                 300

Leu Ile Ser Asn Ile Asn Val Ile Val Leu Glu Leu Lys Gly Ser Glu
305                 310                 315                 320

Thr Thr Phe Met Cys Glu Tyr Ala Asp Glu Thr Ala Thr Ile Val Glu
                325                 330                 335

Phe Leu Asn Arg Trp Ile Thr Phe Cys Trp Ser Ile Ile Ser Thr Leu
            340                 345                 350

Thr

<210> SEQ ID NO 11
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gln Val Gln Leu
    210                 215                 220

Gln Gln Ser Gly Ala Glu Leu Ala Arg Pro Gly Ala Ser Val Lys Met
225                 230                 235                 240

Ser Cys Lys Ala Ser Gly Tyr Thr Phe Thr Arg Tyr Thr Met His Trp
            245                 250                 255

Val Lys Gln Arg Pro Gly Gln Gly Leu Glu Trp Ile Gly Tyr Ile Asn
        260                 265                 270

Pro Ser Arg Gly Tyr Thr Asn Tyr Asn Gln Lys Phe Lys Asp Lys Ala
    275                 280                 285

Thr Leu Thr Thr Asp Lys Ser Ser Thr Ala Tyr Met Gln Leu Ser
        290                 295                 300

Ser Leu Thr Ser Glu Asp Ser Ala Val Tyr Tyr Cys Ala Arg Tyr Tyr
305                 310                 315                 320

Asp Asp His Tyr Cys Leu Asp Tyr Trp Gly Gln Gly Thr Thr Leu Thr
            325                 330                 335

Val Ser Ser Gly Gly Gly Gly Ser Gly Gly Gly Gly Ser Gly Gly Gly
        340                 345                 350

Gly Ser Asp Ile Gln Ile Val Leu Thr Gln Ser Pro Ala Ile Met Ser
    355                 360                 365

Ala Ser Pro Gly Glu Lys Val Thr Met Thr Cys Ser Ala Ser Ser Ser
370                 375                 380

Val Ser Tyr Met Asn Trp Tyr Gln Gln Lys Ser Gly Thr Ser Pro Lys
385                 390                 395                 400

Arg Trp Ile Tyr Asp Thr Ser Lys Leu Ala Ser Gly Val Pro Ala His
            405                 410                 415

Phe Arg Gly Ser Gly Ser Gly Thr Ser Tyr Ser Leu Thr Ile Ser Gly
        420                 425                 430

Met Glu Ala Glu Asp Ala Ala Thr Tyr Tyr Cys Gln Gln Trp Ser Ser
    435                 440                 445

Asn Pro Phe Thr Phe Gly Ser Gly Thr Lys Leu Glu Ile Asn
    450                 455                 460

<210> SEQ ID NO 12
<211> LENGTH: 469
<212> TYPE: PRT
<213> ORGANISM: Artificial Sequence
<220> FEATURE:
<223> OTHER INFORMATION: Synthetic Polypeptide

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Leu Gly Val Tyr Phe Cys Ser Gln Ser
            85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Ala Pro Thr Ser
            210                 215                 220

Ser Ser Thr Gln Val Gln Leu Gln Gln Ser Gly Ala Glu Leu Ala Arg
225                 230                 235                 240

Pro Gly Ala Ser Val Lys Met Ser Cys Lys Ala Ser Gly Tyr Thr Phe
            245                 250                 255

Thr Arg Tyr Thr Met His Trp Val Lys Gln Arg Pro Gly Gln Gly Leu
            260                 265                 270

Glu Trp Ile Gly Tyr Ile Asn Pro Ser Arg Gly Tyr Thr Asn Tyr Asn
            275                 280                 285

Gln Lys Phe Lys Asp Lys Ala Thr Leu Thr Thr Asp Lys Ser Ser Ser
290                 295                 300

Thr Ala Tyr Met Gln Leu Ser Ser Leu Thr Ser Glu Asp Ser Ala Val
305                 310                 315                 320

Tyr Tyr Cys Ala Arg Tyr Tyr Asp Asp His Tyr Cys Leu Asp Tyr Trp
            325                 330                 335

Gly Gln Gly Thr Thr Leu Thr Val Ser Ser Gly Gly Gly Gly Ser Gly
            340                 345                 350

Gly Gly Gly Ser Gly Gly Gly Gly Ser Asp Ile Gln Ile Val Leu Thr
            355                 360                 365

Gln Ser Pro Ala Ile Met Ser Ala Ser Pro Gly Glu Lys Val Thr Met
            370                 375                 380

Thr Cys Ser Ala Ser Ser Ser Val Ser Tyr Met Asn Trp Tyr Gln Gln
385                 390                 395                 400

Lys Ser Gly Thr Ser Pro Lys Arg Trp Ile Tyr Asp Thr Ser Lys Leu
            405                 410                 415

Ala Ser Gly Val Pro Ala His Phe Arg Gly Ser Gly Ser Gly Thr Ser
            420                 425                 430

Tyr Ser Leu Thr Ile Ser Gly Met Glu Ala Glu Asp Ala Ala Thr Tyr
            435                 440                 445

Tyr Cys Gln Gln Trp Ser Ser Asn Pro Phe Thr Phe Gly Ser Gly Thr
            450                 455                 460

Lys Leu Glu Ile Asn
465

<210> SEQ ID NO 13
<211> LENGTH: 133
```

```
<212> TYPE: PRT
<213> ORGANISM: Artificial Sequence
<220> FEATURE:
<223> OTHER INFORMATION: Synthetic Polypeptide

<400> SEQUENCE: 13

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130
```